(12) United States Patent
Chen

(10) Patent No.: US 7,232,825 B2
(45) Date of Patent: Jun. 19, 2007

(54) PHENYLAMINOPYRIMIDINE DERIVATIVES AND METHODS OF USE

(76) Inventor: Guoqing P Chen, 515 Oakbury Ct., Thousand Oaks, CA (US) 91360

( * ) Notice: Subject to any disclaimer, the term of this patent is extended or adjusted under 35 U.S.C. 154(b) by 384 days.

(21) Appl. No.: 10/821,382

(22) Filed: Apr. 9, 2004

(65) Prior Publication Data

US 2004/0224967 A1 Nov. 11, 2004

Related U.S. Application Data

(60) Provisional application No. 60/466,883, filed on May 2, 2003.

(51) Int. Cl.
*C07D 401/02* (2006.01)
*A61K 31/505* (2006.01)

(52) U.S. Cl. .................. 514/252.18; 514/275; 544/331

(58) Field of Classification Search ................ 544/331; 514/252.18, 275
See application file for complete search history.

(56) References Cited

FOREIGN PATENT DOCUMENTS

WO WO 2004/029038 * 4/2004
WO WO 2004/099186 * 11/2004

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*

* cited by examiner

*Primary Examiner*—Deepak Rao

(57) ABSTRACT

The present invention relates to phenylaminopyrimidine derivatives, processes for their preparation, pharmaceutical compositions containing them as active ingredient, methods for the treatment of disease states such as cancers associated with tyrosine kinases, especially Bcr-Abl, to their use as medicaments and to their use in the manufacture of medicaments for use in the production of inhibition of tyrosine kinase reducing effects in warm-blooded animals such as humans.

9 Claims, No Drawings

PHENYLAMINOPYRIMIDINE DERIVATIVES AND METHODS OF USE

This application claims the benefit of U.S. Provisional Application No. 60/466,883 filed on May 2, 2003.

FIELD OF THE INVENTION

The present invention relates to phenylaminopyrimidine derivatives, processes for their preparation, pharmaceutical compositions containing them as active ingredient, methods for the treatment of disease states such as cancers associated with tyrosine kinases, especially Bcr-Abl, to their use as medicaments and to their use in the manufacture of medicaments for use in the production of inhibition of tyrosine kinase reducing effects in warm-blooded animals such as humans.

BACKGROUND OF THE INVENTION

Protein tyrosine kinases have been identified as key players in cellular regulation. They are involved in immune, endocrine, and nervous system physiology and pathology and thought to be important in the development of many cancers. Tyrosine kinases catalyze the transfer of the gamma-phosphoryl group from ATP to tyrosine hydroxyls of proteins. It modulates a wide variety of cellular events, including differentiation, growth, metabolism and apoptosis.

Protein tyrosine kinases represent a diverse and rapidly expanding superfamily of protein, including both transmembrane receptor tyrosine kinases and soluble cytoplasmic enzymes also known as nonreceptor tyrosine kinases. Receptor-type protein tyrosine kinases, which have a transmembrane topology, have been studied extensively. The binding of a specific ligand to the extracellular domain of receptor protein tyrosine kinases is thought to induce receptor dimerization and phosphorylation of their own tyrosine residues. The intracellular, cytoplasmic, non-receptor protein tyrosine kinases may be broadly defined as those protein tyrosine kinases, which do not contain a hydrophobic, transmembrane domain. Within this broad classification, one can divide the known cytoplasmic protein tyrosine kinases into four distinct morphotypes: the SRC family, the FES family, the JAK family and the ABL family. While distinct in their overall molecular structure, each of the members of these morphotypic families of cytoplasmic protein tyrosine kinases share non-catalytic domains in addition to sharing their catalytic kinase domains.

The ABL proto-oncogene normally encodes a protein with tyrosine kinase activity. This activity is augmented in cells carrying bcr-abl hybrid genes. The BCR-ABL protein tyrosine kinase oncoprotein may transform cells via changes in enzyme activity and/or altering of noncovalent protein-protein interactions. The gene encoding the BCR-ABL oncoprotein is a chimeric oncogene generated by the translocation of sequences from the cABL protein tyrosine kinase on chromosome 9 into BCR sequences on chromosome 22 (reviewed in Kurzock et al., 1988, N. Enql. J. Med. 319: 990-998, and Rosenberg et al., 1988, Adv. in Virus Res. 35:39-81). The BCR-ABL oncogene has been implicated in the pathenogenesis of Philadelphia chromosome (Ph@1) positive human leukemias. Namely, the Ph@1 chromosome is found in at least 90 to 95 percent of cases of chronic myelogenous leukemia (CML), which is a clonal cancer arising from the neoplastic transformation of hematopoietic stem cells (Fialkow et al., 1977, Am. J. Med. 63:125-130), and is also observed in approximately 20 percent of adults with acute lymphocytic leukemia (ALL), 5 percent of children with ALL, and 2 percent of adults with acute myelogenous leukemia (AML) (Whang-Peng et al., 1970, Blood 36:448-457; Look, A. T., 1985, Semin. Oncol. 12:92-104). The BCR-ABL gene produces two alternative chimeric proteins, P210 BCR-ABL, and P185 BCR-ABL, which are characteristic of CML and ALL, respectively. Further, it has recently been directly demonstrated that the BCR-ABL gene product is the causative agent in CML (Skorski et al., 1993, J. Clin Invest. 92:194-202; Snyder et al., 1993, Blood 82:600-605).

Two major types of bcr-abl translocations are known, characterized by two different bcr-abl junctions. One translocation is between bcr exon 2 and abl exon 2, while another translocation is between bcr exon 3 and the same abl exon 2 (Shtivelman et al., Cell 47, 277-284 (1986)). The two types of junction have been referred to as the "L-6" (or "b2a2") and "K-28" (or "b3a2") junctions, respectively. The alternative splicing from two bcr-abl exons to the abl coding sequence results in two different bcr-abl fusion proteins, one including the 25 amino acids encoded by bcr exon 3 and one which lacks those amino acids. One or both of these junctions is detected in Ph@1 -positive CML patients (Shtivelman et al., Blood 69, 971 (1986)).

It has now been founded that phenylaminopyrimidine derivatives of formula (I), described below, are a new class of compounds that have advantageous pharmacological properties and inhibit the activity of tyrosine kinases, for example, the activity of the BCR-ABL tyrosine kinase, the activity of other receptor tyrosine kinases, such as PDGF.

On the basis of the described properties, is thus suitable for the treatment of Bcr-Abl-positive cancer and tumor diseases, such as leukaemias (especially chronic myeloid leukaemia and acute lymphoblastic leukaemia, where especially apoptotic mechanisms of action are found), and also shows effects on the subgroup of leukaemic stem cells as well as potential for the purification of these cells in vitro after removal of said cells (for example, bone marrow removal) and reimplantation of the cells once they have been cleared of cancer cells (for example, reimplantation of purified bone marrow cells) as well as Gastrointestinal Stromal Tumors (GIST). A compound of formula I may be used not only as a tumor-inhibiting substance, for example in small cell lung cancer, but also as an agent to treat non-malignant proliferative disorders, such as atherosclerosis, thrombosis, psoriasis, scleroderma, and fibrosis, as well as for the protection of stem cells, for example to combat the haemotoxic effect of chemotherapeutic agents, such as 5-fluoruracil, and in asthma. It may especially be used for the treatment of diseases which respond to an inhibition of the PDGF receptor kinase.

In addition, a compound of formula I prevents the development of multidrug resistance in cancer therapy with other chemotherapeutic agents or abolishes a pre-existing resistance to other chemotherapeutic agents. Also regardless of the effect described hereinbefore, a compound of formula I may be used to advantage in combination with other antitumor agents.

Examples of phenylaminopyrimidine derivatives that are similar in structure to those of the present invention are disclosed in the following patent applications: EP 0564409, WO 9509847, WO 9509851, WO 9509852, WO 9509853, WO 0222597.

SUMMARY OF THE INVENTION

The present invention relates to phenylaminopyrimidine derivatives of formula (I)

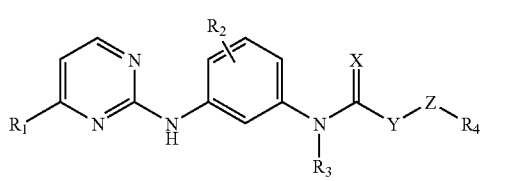

Formula (I)

Wherein

X is oxygen or sulfur,

Y is a direct bond, oxygen, nitrogen or lower alkyl,

Z is an aliphatic, cycloaliphatic, aryl or a heterocyclyl radical, $R_1$ is heterocyclyl radical, $R_2$ is hydrogen, halogen, halogenlower alkyl, lower alkyl or lower alkoxyl, $R_3$ is hydrogen or lower alkyl, $R_4$ is oxy-lower alkylamino, lower alkyl oxy-lower alkylamino, oxyheterocyclyl, lower alkyl oxyheterocyclyl, oxy-lower alkylheterocyclyl, lower alkyl oxy-lower alkylheterocyclyl, halogenlower alkylamino, halogenlower alkylheterocyclyl, amino lower alkylamino, lower alkylamino lower alkylamino, aminoheterocyclyl, lower alkylamino heterocyclyl, amino lower alkylheterocyclyl or lower alkylamino lower alkylheterocyclyl.

or a pharmaceutically acceptable salt thereof.

DETAIED DESCRIPTION OF THE INVENTION

The present invention is the direct to novel compounds which can inhibit protein tyrosine kinases, especially BCR-ABL tyrosine kinase, and use of these compounds for inhibition of tyrosine kinases in the treatment of a neoplastic or proliferative or inflammatory diseases, or transplantation disorders which are all caused by excess or inappropriate tyrosine kinases in a mammal in need thereof.

In the compounds of formula (I):

X is oxygen or sulfur, preferably oxygen,

Y is a direct bond, oxygen, nitrogen or lower alkyl, preferably Y is NH or a direct bond, i.e. Y is not present, Z is an aliphatic, cycloaliphatic, aryl or a heterocyclyl radical comprising one or more ring nitrogen atoms and 0, 1 or 2 heteroatoms independently from each other selected from the group consisting of oxygen and sulfur; preferably phenyl which unsubstituted or substituted with halogen, halogenlower alkyl, lower alkyl or lower alkoxy, cyano, $R_1$ is heterocyclyl radical, preferably heteroaryl group comprising one or more ring nitrogen atoms and 0, 1 or 2 heteroatoms independently from each other selected from the group consisting of oxygen and sulfur, which groups in each case are unsubstituted or mono- or polysubstituted; preferably unsubstituted or substituted 3- or 4-pyridyl, $R_2$ is hydrogen; halogen, preferably fluoro or chloro; halogenlower alkyl, preferably trifloromethyl; lower alkyl, preferably methyl or ethyl; or lower alkoxy, preferably methoxy or ethoxy, $R_3$ is hydrogen or lower alkyl, preferably hydrogen, $R_4$ is oxy-lower alkylamino, lower alkyl oxy-lower alkylamino, oxyheterocyclyl, lower alkyl oxyheterocyclyl, oxy-lower alkylheterocyclyl, lower alkyl oxy-lower alkylheterocyclyl, halogenlower alkylamino, halogenlower alkylheterocyclyl, amino lower alkylamino, lower alkylamino lower alkylamino, aminoheterocyclyl, lower alkylamino heterocyclyl, amino lower alkylheterocyclyl or lower alkylamino lower alkylheterocyclyl;

Preferably $R_4$ is (a) oxy-lower alkyl unsubstituted, mono or disubstituted amino; oxy-lower alkyl morpholinyl, oxy-lower alkyl pyrrolidinyl, oxy-lower alkyl piperidinyl, oxy-lower alkyl piperazinyl, oxy-lower alkyl aminopyridinyl, oxy-pyrrolidinyl, oxy-piperidinyl, (b) lower alkyl oxy-lower alkyl unsubstituted, mono or disubstituted amino; lower alkyl oxy-lower alkyl morpholinyl, lower alkyl oxy-lower alkyl pyrrolidinyl, lower alkyl oxy-lower alkyl piperidinyl, lower alkyl oxy-lower alkyl piperazinyl, lower alkyl oxy-lower alkyl aminopyridinyl, lower alkyl oxy-pyrrolidinyl, lower alkyl oxy-piperidinyl, (c) mono or difluoro substituted lower alkyl unsubstituted, mono or disubstituted amino; mono or difluoro substituted lower alkyl morpholinyl, mono or difluoro substituted lower alkyl pyrrolidinyl, mono or difluoro substituted lower alkyl piperidinyl, mono or difluoro substituted lower alkyl piperazinyl, mono or difluoro substituted lower alkyl aminopyridinyl, (d) amino lower alkyl unsubstituted, mono or disubstituted amino; amino lower alkyl morpholinyl, amino lower alkyl pyrrolidinyl, amino lower alkyl piperidinyl, amino lower alkyl piperazinyl, amino lower alkyl aminopyridinyl, amino pyrrolidinyl, amino piperidinyl, (e) lower alkylamino lower alkyl unsubstituted, mono or disubstituted amino; lower alkylamino lower alkyl morpholinyl, lower alkylamino lower alkyl pyrrolidinyl, lower alkylamino lower alkyl piperidinyl, lower alkylamino lower alkyl piperazinyl, lower alkylamino lower alkyl aminopyridinyl, lower alkylamino pyrrolidinyl, lower alkyl amino piperidinyl.

or a pharmaceutically acceptable salt thereof, preferably methanesulfonic acid salt.

The term "halogen", as used herein, unless otherwise indicated, includes fluoro, chloro, bromo or iodo. Preferred halogens are fluoro and chloro.

The term "halogen-lower alkyl", as used herein, unless otherwise indicated, includes 1 to 6 halogen-substituted alkyl, preferably substituted by fluoro or chloro such as trifluoromethyl.

The term "lower alkyl", as used herein, unless otherwise indicated, includes 1 to 6 saturated monovalent hydrocarbon radicals having straight, branched or cyclic moieties, including, but not limited to, methyl, ethyl, n-propyl, iso-propyl, n-butyl, sec-butyl, tert-butyl, cyclopropyl, cyclobutyl and the like.

The term "lower alkoxy", as used herein, unless otherwise indicated, includes —O-lower alkyl groups wherein lower alkyl is as defined above.

The term "aliphatic", as used herein, unless otherwise indicated, includes at least five carbon atoms preferably has not more than twenty-two carbon atoms, generally not more than ten carbon atoms, it includes substituted or preferably unsubstituted alkynyl, alkenyl or preferably alkyl radical, such as $C_5$-$C_7$ alkyl, for example n-pentyl.

The term "cycloaliphatic", as used herein, unless otherwise indicated, includes especially up to twenty, more especially up to ten carbon atoms, is mono- or poly-cyclic and is substituted or preferably unsubstituted, for example such a cycloalkyl radical, especially such a 5- or 6-membered cycloalkyl radical, such as preferably cyclohexyl.

The term "oxy-lower alkylamino", as used herein, unless otherwise indicated, includes —O-lower alkyl-N groups wherein the nitrogen is unsubstituted, mono- or di-substituted by lower alkyl, aliphatic or cycloaliphatic radicals and lower alkyl, aliphatic and cycloaliphatic are as defined above, such as —OCH$_2$CH$_2$NHCH$_3$.

The term "lower alkyl oxy-lower alkylamino", as used herein, unless otherwise indicated, includes lower alkyl-O-lower alkyl-N groups wherein the nitrogen is unsubstituted, mono- or di-substituted by lower alkyl, aliphatic or cycloaliphatic radicals and lower alkyl, aliphatic and cycloaliphatic are as defined above, such as —CH$_2$OCH$_2$CH$_2$NHCH$_3$.

The term "halogenlower alkylamino", as used herein, unless otherwise indicated, includes 1 to 6 halogen substituted alkylamino groups, preferably substituted by fluoro or chloro, wherein the nitrogen is unsubstituted, mono- or di-substituted by lower alkyl, aliphatic or cycloaliphatic radicals and lower alkyl, aliphatic and cycloaliphatic are as defined above, such as —CF$_2$NHCH$_3$.

The term "aryl", as used herein, unless otherwise indicated, includes an organic radical derived from an aromatic hydrocarbon by removal of one hydrogen, such as phenyl or naphthyl, preferably phenyl, and is unsubstituted or substituted by one or two substituents, selected from halogen, halogen-lower alkyl, lower alkyl, lower alkenyl, lower alkynyl, cyano, lower alkylcyano, hydroxy, lower alkoxy, carboxy, carboxyalkyl, amino, carbamoyl, cabamate, ureido, mercapto, sulfo, lower alkysulfinyl, lower alkanesulfonyl, sulfonamide; aryl includes one aromatic ring fused with an aliphatic ring, such as a saturated or partially saturated ring, such as tetrahydronaphthyl.

The term "heterocyclyl", as used herein, unless otherwise indicated, includes non-aromatic, single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. Examples of heterocyclyl groups include pyrrolidine, pyrrolidione, piperidine, piperidinone, piperazine, morpholine, imidazolidine, pyrazolidine and hydantoin, pyrrole, indole, pyrazole, indazole, trizole, benzotrizole, imidazole, benzoimdazole, thiophene, benzothiophene, thiozole, benzothiozole, furan, benzofuran, oxazole, bezoxazole, isoxazole, tetrazole, pyridine, pyrimidine, trizine, quinoline, isoquinoline, quinazoline, indoline, indolinone, benzotetrahydrofuran, tetrahydroquinoline, tetrahydroisoquinoline, methylenedioxyphenyl. The heterocyclic and heterocyclic rings may be optionally substituted and substituents selected from the group defined above as substituents for aryl.

The term "oxyheterocyclyl", as used herein, unless otherwise indicated, includes —O-heterocyclyl wherein oxygen is substituted on any desired heterocyclyl ring position preferably substituted on ring carbon atom and, heterocyclyl is as defined above, such as —O-piperidinyl.

The term "lower alkyl oxyheterocyclyl", as used herein, unless otherwise indicated, includes—lower alky-O-heterocyclyl wherein oxygen is substituted on any desired heterocyclyl ring position preferably substituted on ring carbon atom and, lower alkyl and heterocyclyl are as defined above, such as —CH$_2$O-piperidinyl.

The term "oxy-lower alkylheterocyclyl", as used herein, unless otherwise indicated, includes —O-lower alkyl-heterocyclyl wherein oxygen is substituted on lower alkyl that substituted on any desired heterocyclyl ring position preferably substituted on ring carbon atom and, lower alkyl and heterocyclyl are as defined above, such as —OCH$_2$-piperidinyl.

The term "lower alkyl oxy-lower alkylheterocyclyl", as used herein, unless otherwise indicated, includes—lower alkyl-O-lower alkyl-heterocyclyl wherein oxygen is substituted on lower alkyl that substituted on any desired heterocyclyl ring position preferably substituted on ring carbon atom and, lower alkyl and heterocyclyl are as defined above, such as —CH$_2$OCH$_2$-piperidinyl.

The term "halogenlower alkylheterocyclyl", as used herein, unless otherwise indicated, includes 1 to 6 halogen substituted alkylheterocyclyl groups, preferably substituted by fluoro or chloro, wherein lower alky and heterocyclyl are as defined above, such as —CF$_2$CH$_2$-piperazinyl and —CF$_2$CH$_2$-piperidinyl.

The term "amino lower alkylamino", as used herein, unless otherwise indicated, includes —N$_1$-lower alkyl-N$_2$ groups wherein the amino nitrogen N$_1$ is substituted by hydrogen, lower alkyl, aliphatic or cycloaliphatic radicals, and the amino nitrogen N$_2$ is unsubstituted, mono or di-substituted by lower alkyl, aliphatic or cycloaliphatic radicals and lower alkyl, aliphatic and cycloaliphatic are as defined above, such as —NHCH$_2$CH$_2$NHCH$_3$.

The term "lower alkylamino lower alkylamino", as used herein, unless otherwise indicated, includes—lower alkyl-N$_1$-lower alkyl-N$_2$ groups wherein the amino nitrogen N$_1$ is substituted by hydrogen, lower alkyl, aliphatic or cycloaliphatic radicals, and the amino nitrogen N$_2$ is unsubstituted, mono or di-substituted by lower alkyl, aliphatic or cycloaliphatic radicals and lower alkyl, aliphatic and cycloaliphatic are as defined above, such as —CH$_2$NHCH$_2$CH$_2$NHCH$_3$.

The term "aminoheterocyclyl", as used herein, unless otherwise indicated, includes —N-heterocyclyl wherein the nitrogen is substituted on any desired heterocyclyl ring position preferably substituted on ring carbon atom, and the amino nitrogen is substituted by hydrogen, lower alkyl, aliphatic or cycloaliphatic radicals, and lower alkyl, aliphatic, cycloaliphatic and heterocyclyl are as defined above, such as —NH-piperidinyl.

The term "lower alkylamino heterocyclyl", as used herein, unless otherwise indicated, includes —lower alkyl-N-heterocyclyl wherein the nitrogen is substituted on any desired heterocyclyl ring position preferably substituted on ring carbon atom, and the amino nitrogen is substituted by hydrogen, lower alkyl, aliphatic or cycloaliphatic radicals, and lower alkyl, aliphatic, cycloaliphatic and heterocyclyl are as defined above, such as —CH$_2$NH-piperidinyl.

The term "amino lower alkylheterocyclyl", as used herein, unless otherwise indicated, includes —N-lower alkylheterocyclyl wherein the lower alkyl is substituted on any desired heterocyclyl ring position, and the amino nitrogen is substituted by hydrogen, lower alkyl, aliphatic or cycloaliphatic radicals, and lower alkyl, aliphatic, cycloaliphatic and heterocyclyl are as defined above, such as —NHCH$_2$CH$_2$-piperidinyl.

The term "lower alkylamino lower alkylheterocyclyl", as used herein, unless otherwise indicated, includes —lower alkyl-N-lower alkylheterocyclyl wherein the lower alkyl of lower alkylheterocyclyl is substituted on any desired heterocyclyl ring position, and the amino nitrogen is substituted by hydrogen, lower alkyl, aliphatic or cycloaliphatic radicals, and lower alkyl, aliphatic, cycloaliphatic and heterocyclyl are as defined above, such as —CH$_2$NHCH$_2$CH$_2$-piperidinyl.

Several in vitro tyrosine kinase inhibition activities can be measured according to following publications: E. Andrejauskas et al., Cancer Research 52, 5353-5358 (1992), Trinks et al., J. Med. Chem. 37, 1015-27 (1994), N. Lydon et al., Oncogene Research 5, 161-173 (1990) and J. F. Geissler et al., Cancer Research 52, 4492-8 (1992).

Typical in vitro and in vivo assays are similarly carried out according to the procedures described by P. L. Coutre et al., Journal of the National Cancer Institute 91 (2), 163-168 (1999).

A compound of formula (I) can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

A compound of formula (I) can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula (I). Suitable pharmaceutically acceptable salts will be apparent to those skilled in the art and include those described in *J. Pharm. Sci.*, 1977, 66, 1-19, such as acid addition salts formed with inorganic acid e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts may be used, for example in the isolation or purification of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extents to all isomeric forms including stereoisomers and geometic isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula (I). Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula (I) may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula (I) and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disstearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods know to those skilled in the art (see, for example: Chien; "transdermal Controlled Systemic Medications"; Marcel Dekker, Inc.; 1987. Lipp et al. WO 94/04157 3 Mar. 1994).

Compounds of general Formula (I) may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula (I), the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.01 to 200 mg/Kg. The daily inhalation dosage regimen will preferably be from 0.01 to 200 mg/Kg of total body weight.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120-1127).

Representative illustrations of the preparation of the present invention are given in Schemes I to XI. Those having skill in the art will recognize that the starting materials may be varied and additional steps may be employed to produce compounds encompassed by the present invention.

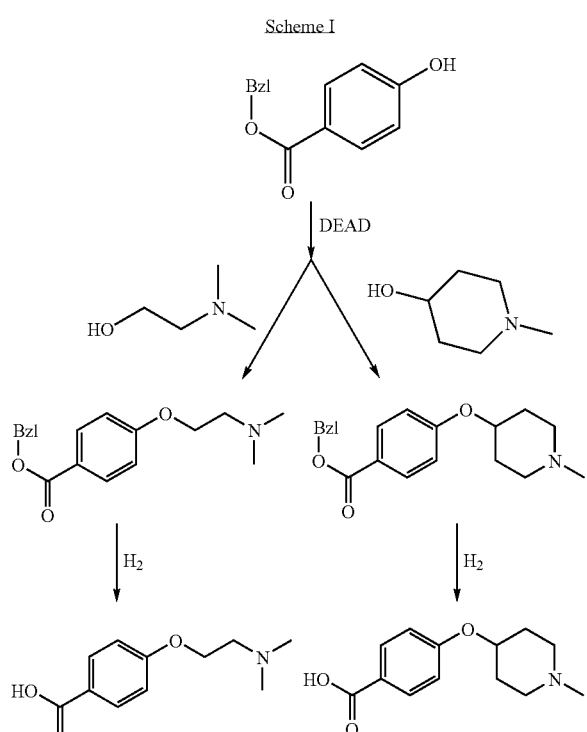

Benzyl 4-hydroxybenzonate can be reacted with various aminoalkyl alcohols, cycloalkylamino alcohols and herteroamino alcohols to undergo Mitsunobu reaction with the catalysis of DEAD (Diethyl azodicarboxylate) to form the ether linkages. The benzyl protecting group can be removed under hydrogen atmosphere to generate the final intermediates in Scheme I for the future reactions.

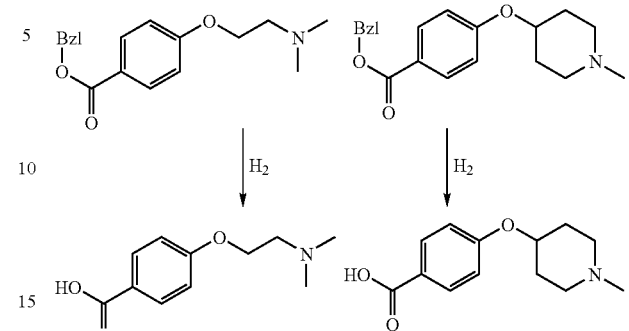

Various aminoalkyl alcohols, cycloalkylamino alcohols and herteroamino alcohols could be reacted with p-toluenesofonyl chloride under basic condition at temperature 50° C.-150° C. to form various tosylates that can be reacted with benzyl 4-hydroxybenzonate in DMF under basic condition to fulish the ether linkage. The benzyl protecting group can be removed under hydrogen atmosphere to generate the final intermediates in Scheme II for the future reactions.

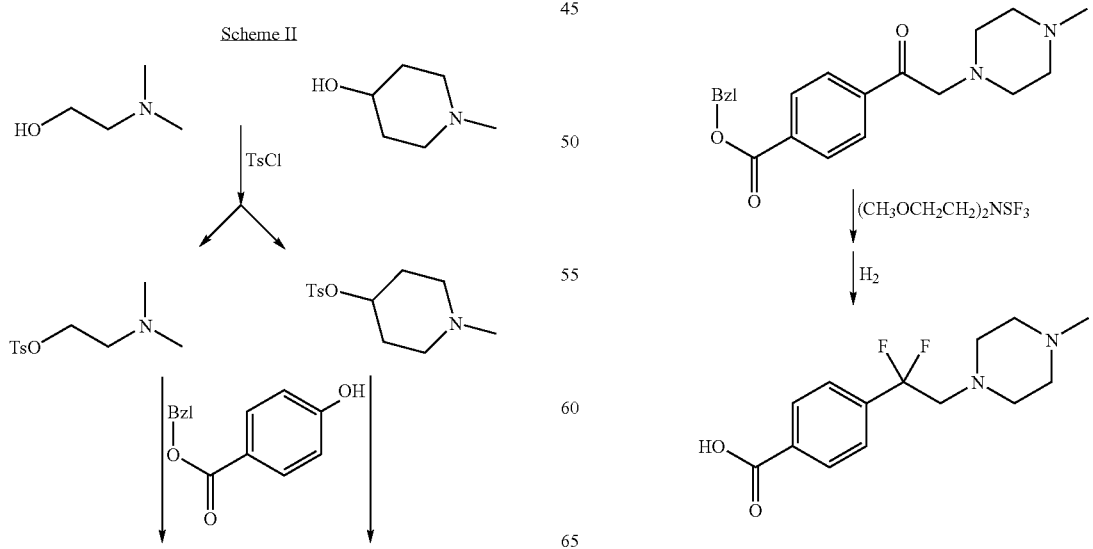

Benzyl 4-acetylbenzonate can be brominated with one equivalent bromine in chloroform to form Benzyl 4-(2'-bromo)acetylbenzonate that can be reacted with various alkyl or cycloalkylamine to generate amino-CH$_2$-carbonyl side chain. The products can be fluorinated with (CH$_3$OCH$_2$CH$_2$)$_2$NSF$_3$ (Gauri S. Lal et al, J. Org. Chem. 1999, 64, 7048-7054) followed by hydrogenation of removal of protecting benzyl group to furnish the final intermediate in Scheme III for the future reactions.

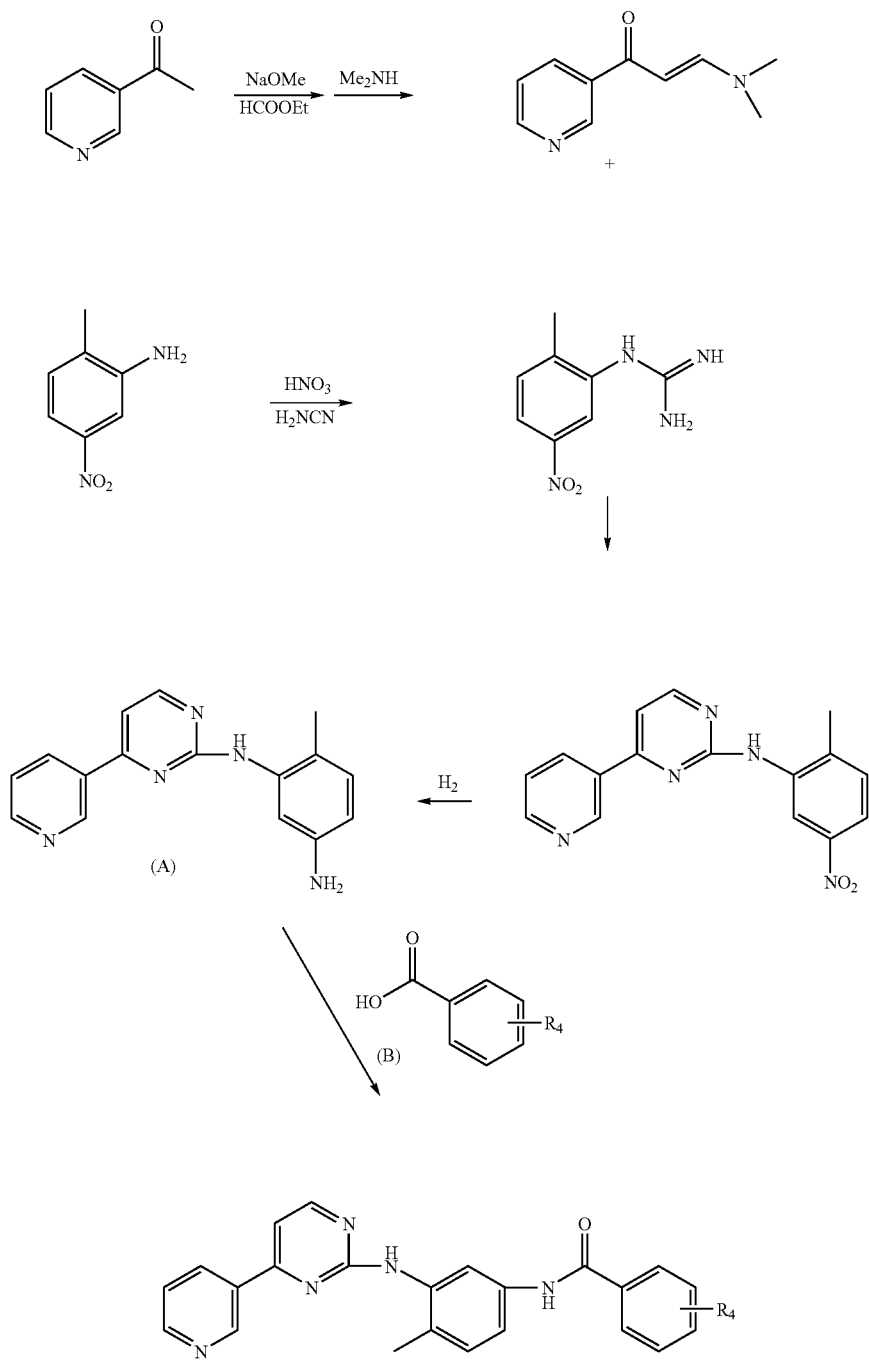

Compound (A) can be made through the above chemistry (U.S. Pat. No. 5,521,184). Compound (B) represents all the final intermediates from Scheme I, Scheme II and Scheme III. (A) and (B) can be reacted with both one equivalent EDC [1-(3-dimethyl-aminopropyl)-3-ethylcarbodiimide hydrochloride] and HOBt (1-hydroxybenzotriazole) in a suitable solvent to form the final products.
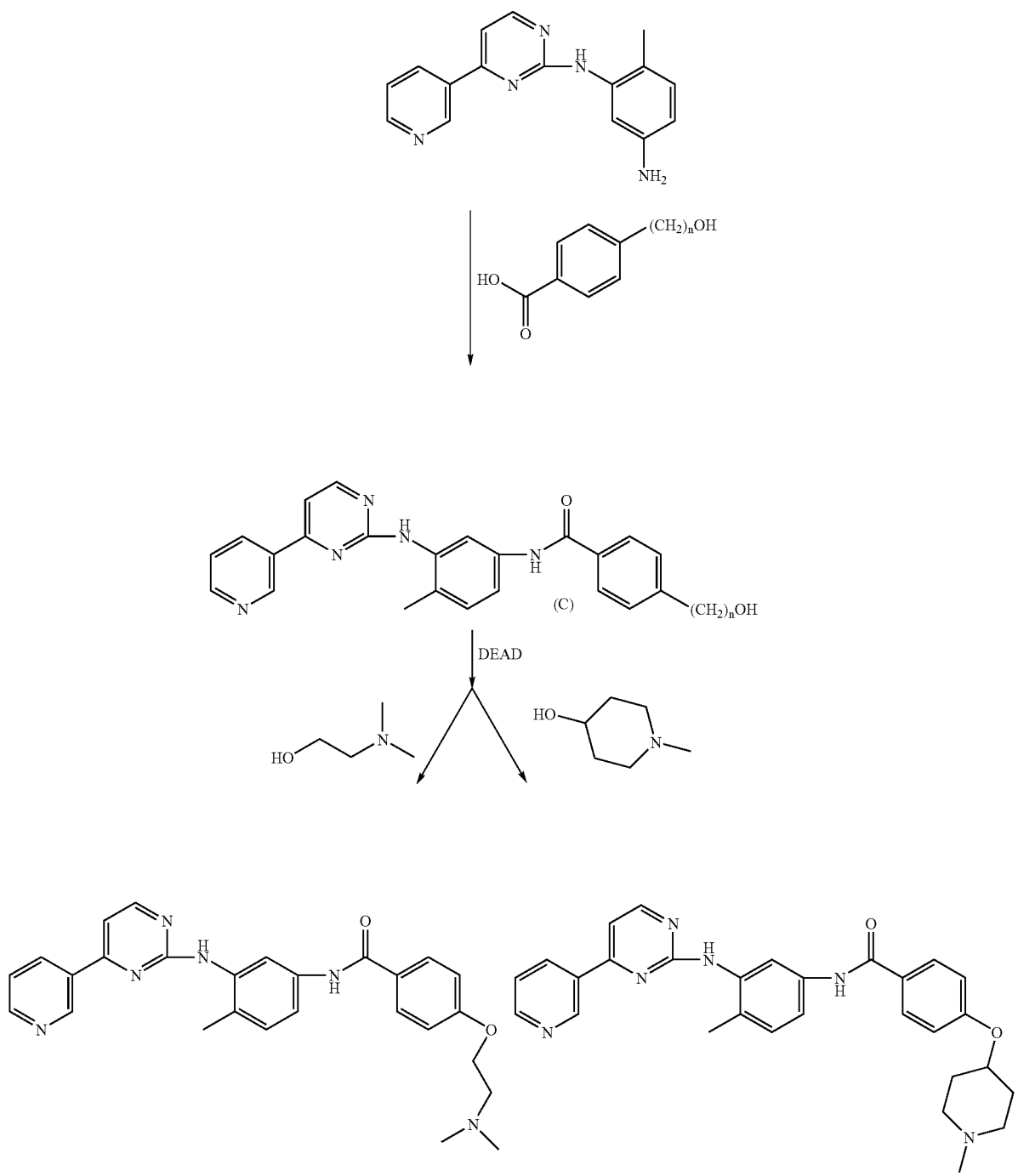

The first step can be conducted according to the similar methods described in Scheme IV at the presence of EDC and HOBt to generate (C) while n is 0. The second step can be furnished similar to the description in Scheme I via the Mitsunobu reaction.
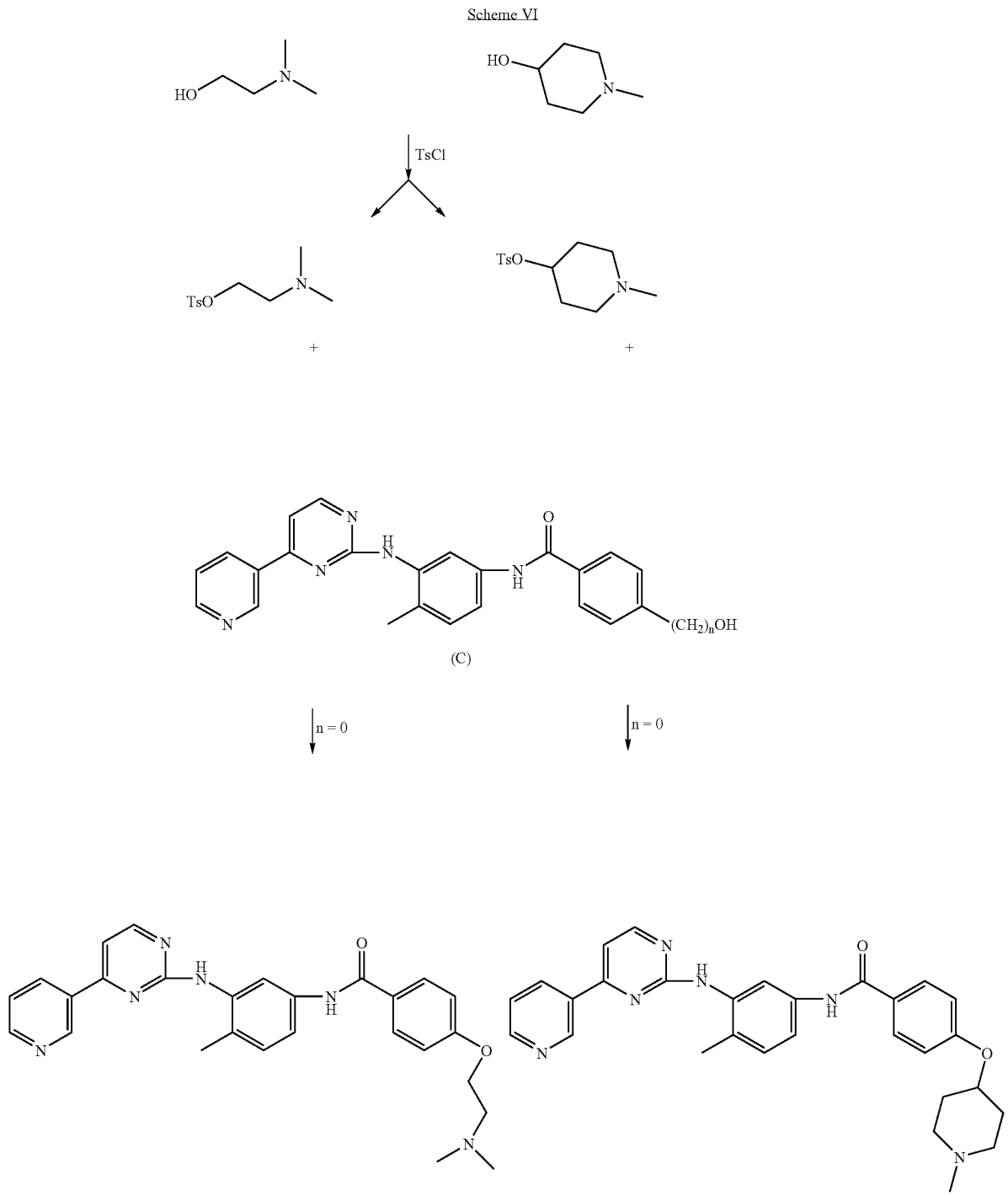
Scheme VI The above reactions can be conducted according to the similar condition described in Scheme II. Compound (C) is the same intermediate as in Scheme V. Similar chemistries can be conducted when n is 1 or 2 to generate the corresponding analogues.
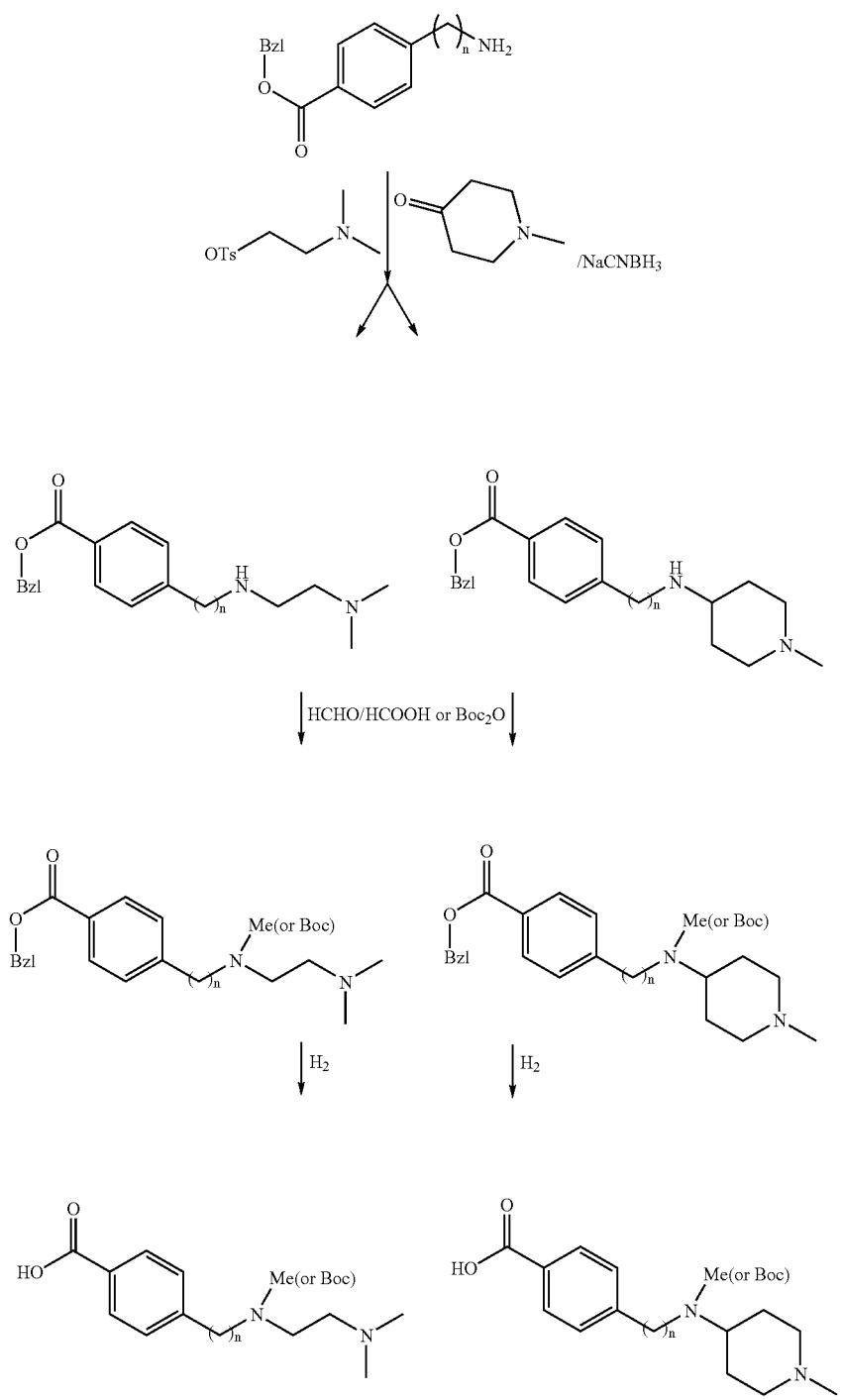
Scheme VII
n = 0, 1, 2, 3

Aminoalkyltosylate can be made from aminoalkylhydroxy and TsCl in basic condition, then undergo displacement and methylation or Boc-acylation followed by hydrogenation. Reductive amination can be used for the preparation of secondary amine as well.

Scheme VIII

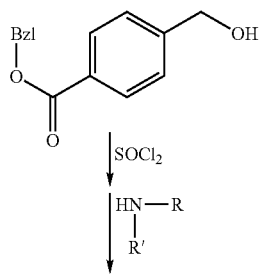

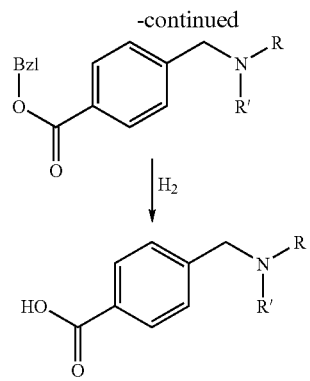

Benzylalchohol can be converted into chloride by SOCl$_2$ and undergo the displacement with amines followed by hydrogenation. R and R' can be hydrogen, lower alkyl, aliphatic cycloaliphatic or heterocyclyl radicals, and lower alkyl, aliphatic, cycloaliphatic and heterocyclyl are as defined above.

Scheme IX

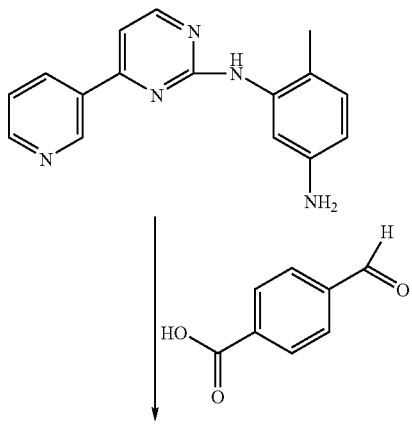

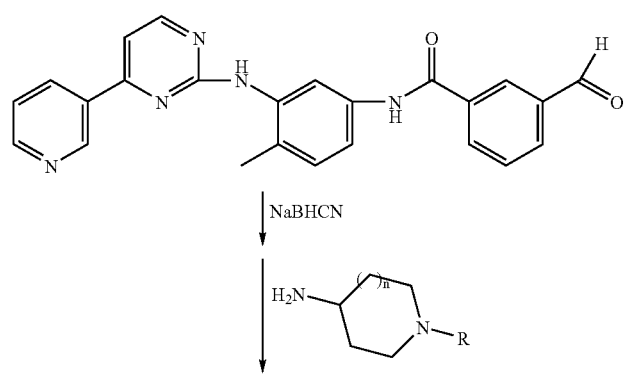

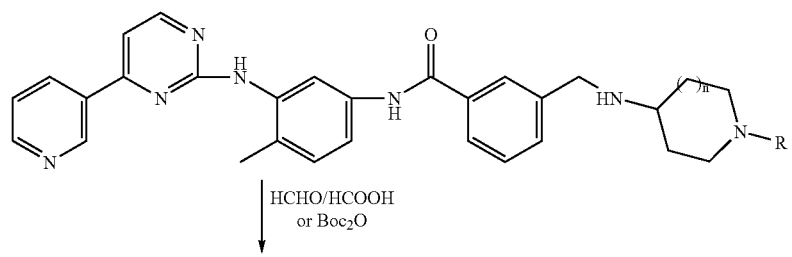

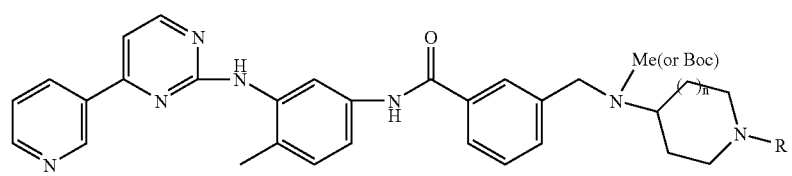

n = 0, 1, 2, 3

Formylbenoic acid was coupled with (A) and derivatized by reductive amination with various amines to give the desired products that could be methylated or protected by Boc for further making analogues.

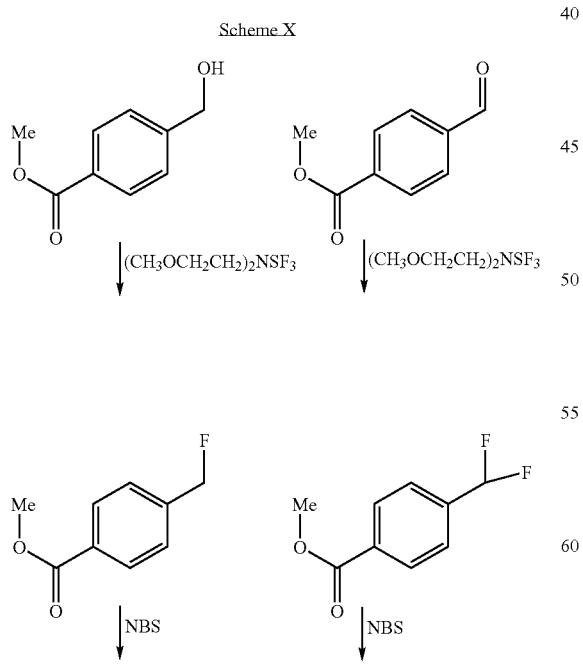

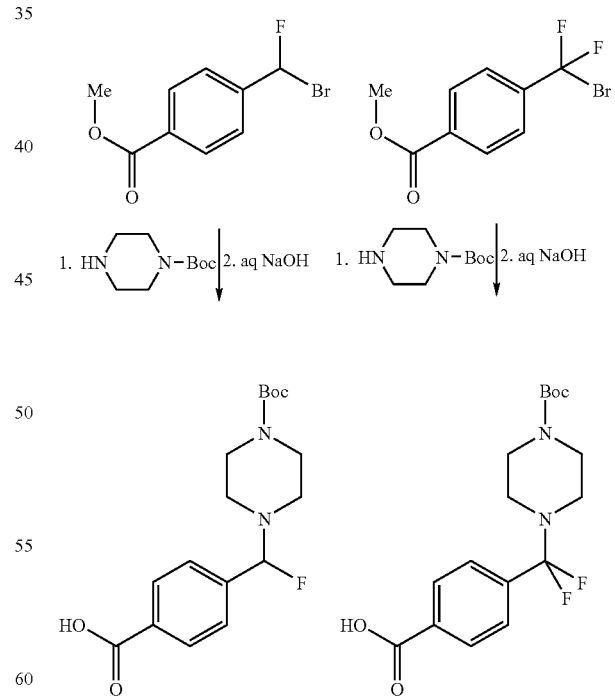

Starting material was fluorinated first followed by bromination with NBS. The resulting product can reacted with various amines and further hydrolyzed to coupled with (A) to give the desired final products.

Scheme XI

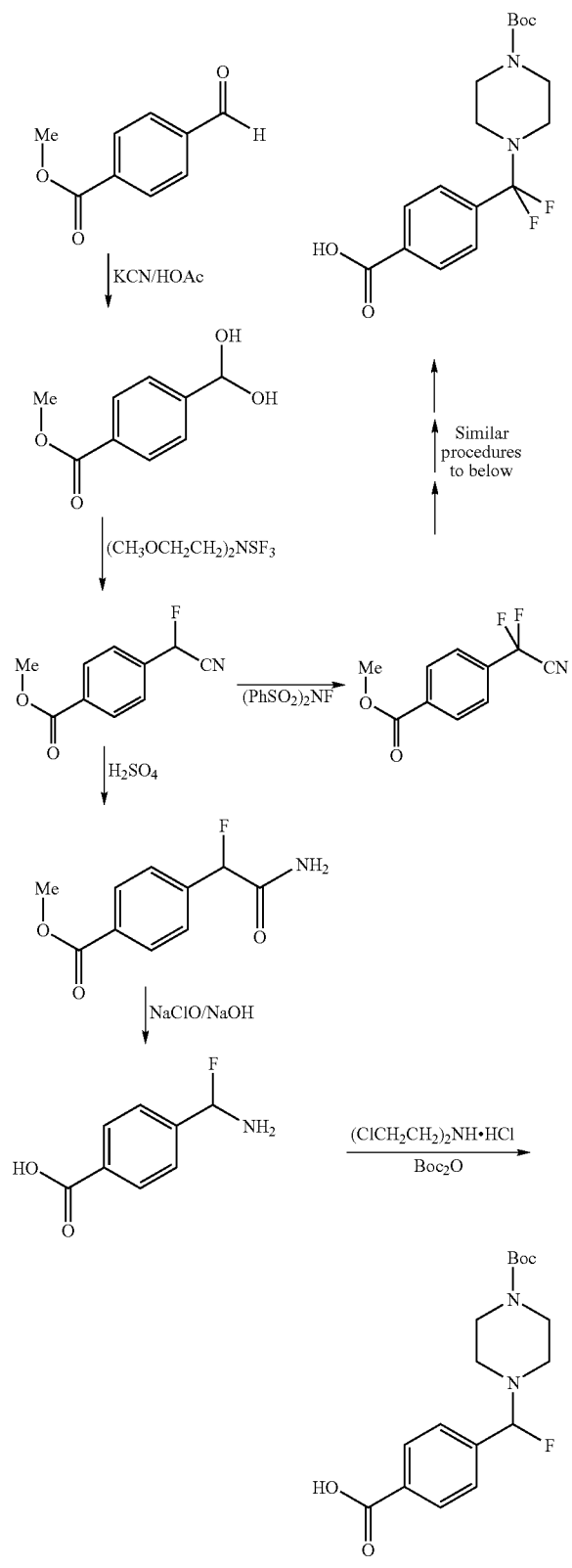
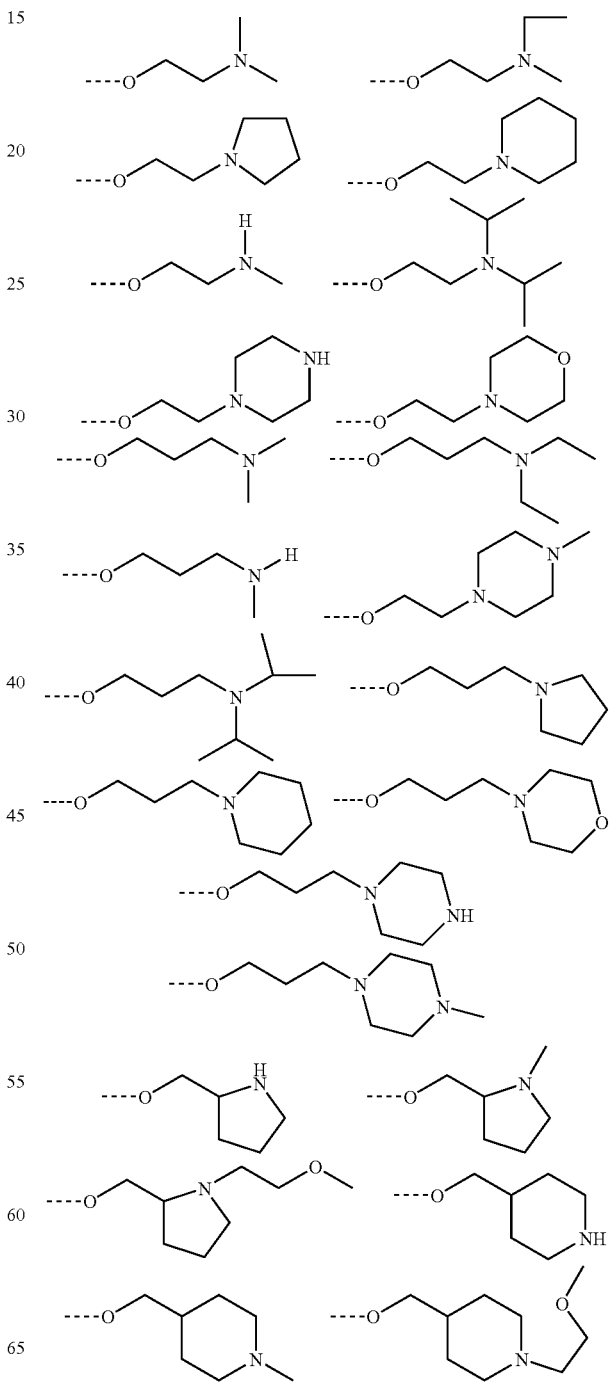

Starting material can be reacted with KCN to form secondary alcohol, which can be fluorinated and further hydrolyzed followed by rearrangement to give the primary amine. It can be cyclized to furnish to six memberd ring system.

The following examples of Formula I, wherein

X is oxygen, Y is a direct bond, Z is phenyl, $R_1$ is: 3-pyridyl or 4-pyridyl $R_2$ is: methyl, F, Cl or hydrogen, $R_3$ is hydrogen, preferably represented by formula II, but not limited, can be prepared similarly according to the methods described in Scheme I-Scheme XI.

$R_4$ is:

-continued
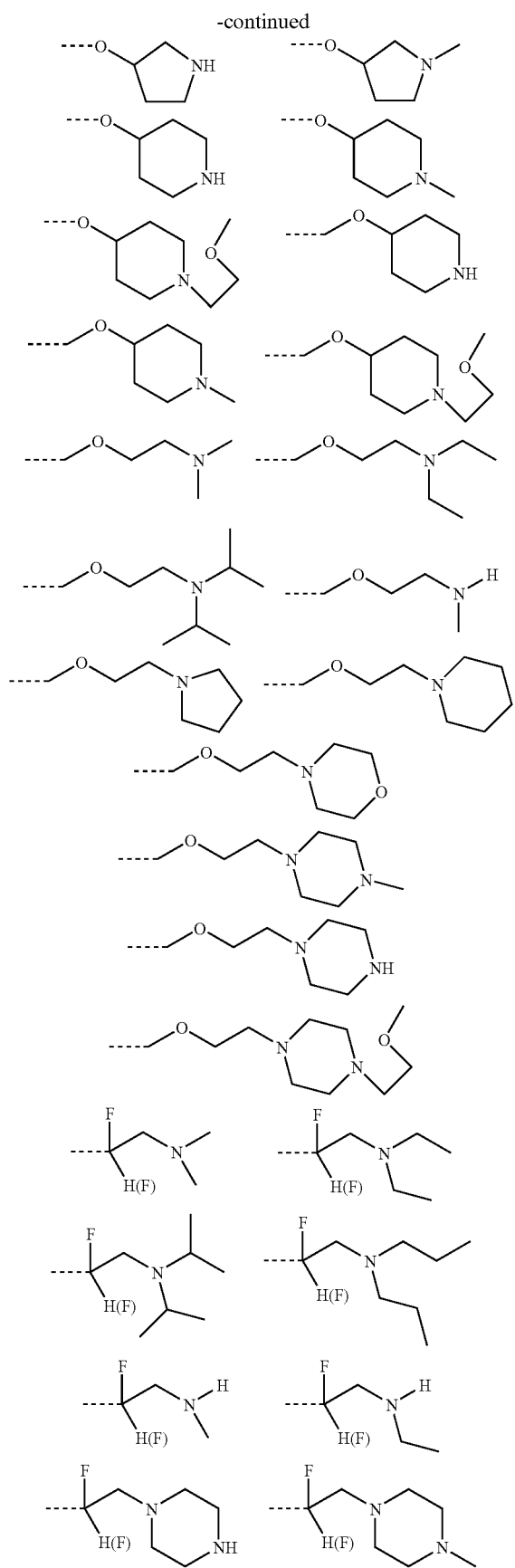
-continued
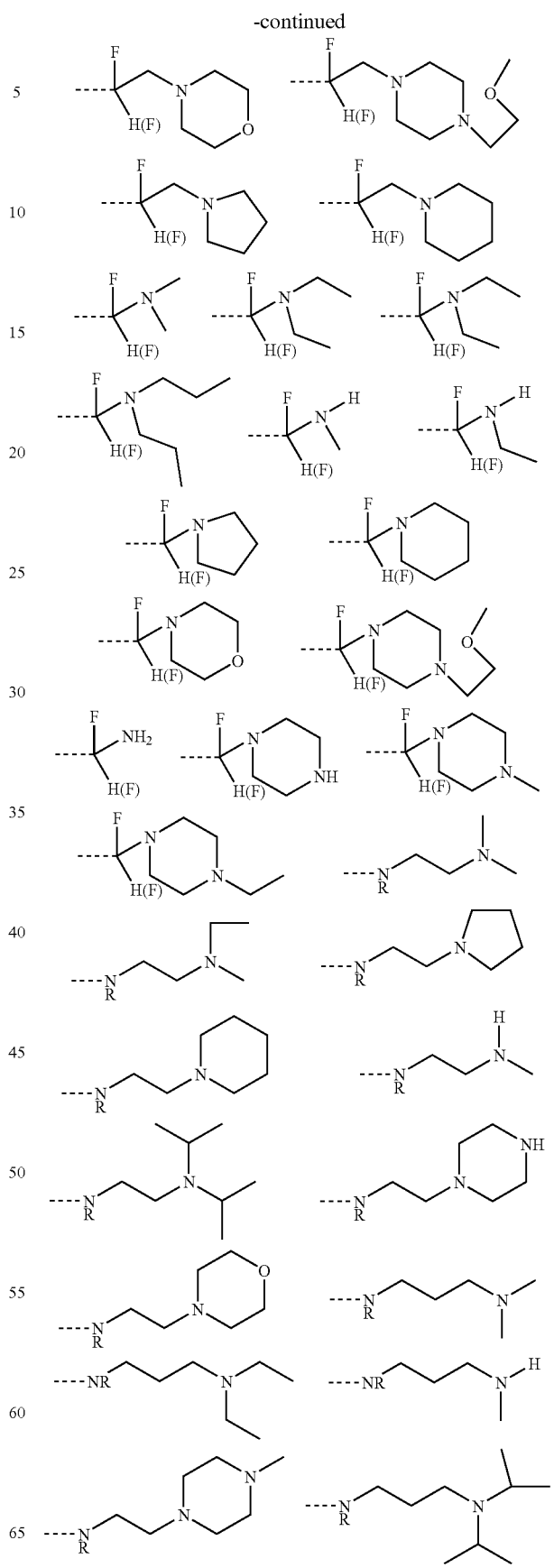

-continued

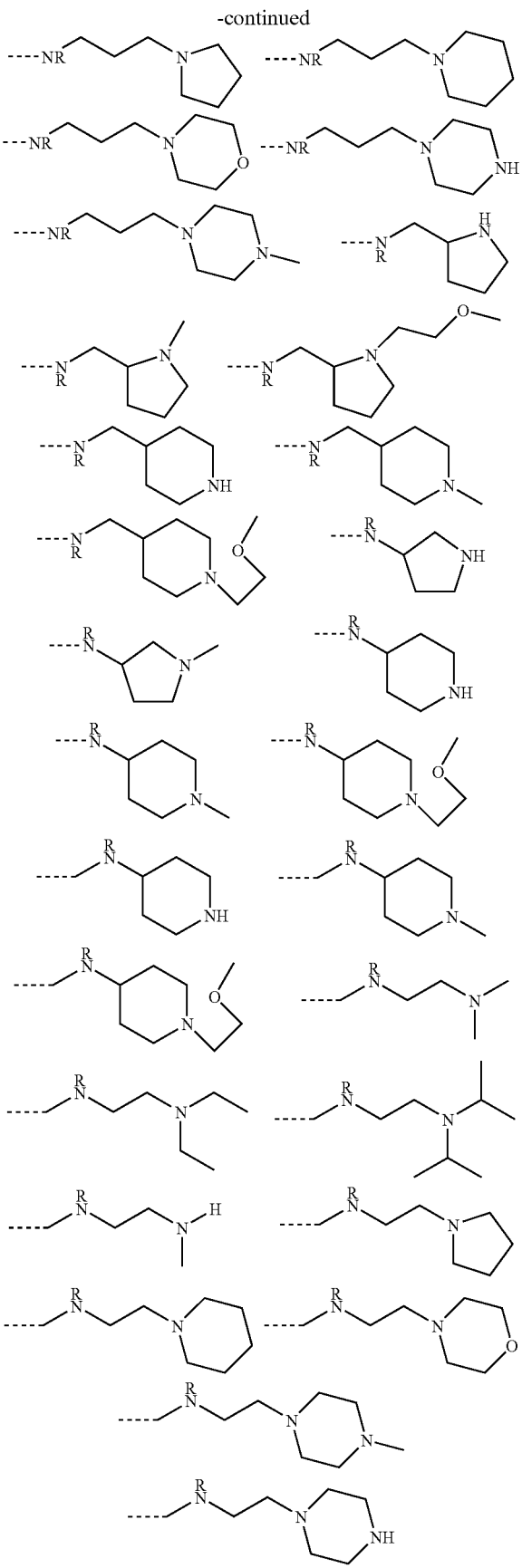
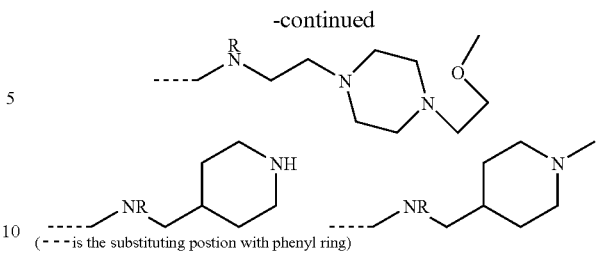

(- - - - is the substituting postion with phenyl ring)

R is hydrogen, lower alkyl, aliphatic, cycloaliphatic or heterocyclyl radicals.

or a pharmaceutically acceptable salt thereof.

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in there entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well known synthetic methods.

Representative methods for preparing intermediates of the invention are set forth below in the examples. All the examples can be made as pharmaceutical acceptable salts, preferabably as methanesulfonic acid salt.

The following abbreviation have been used and others are all standard chemical formula representation.

EtOH: ethanol, RT: room temperature, TEA: triethylamine,

EDCI: 1-(3-dimethylaminopropyl)-3-ethylcarbodiimide hydrochloride,

HOBt: 1-hydroxybenzotriazole hydrate, EtOAc: ethyl acetate,

THF: tetrahydrofuran, MeI: methyl iodide,

DIEA: diisopropylethylamine, DMSO: dimethylsulfoxide, eq: equivalent, g: gram, ml: milliliter, TLC: thin layer chromatography, DEAD: Diethyl azodicarboxylate, DCM: Dichloromethane, Boc: t-Butoxycarbonyl, Preparation I: N-(5-amino-2-methylphenyl)-4-(3-pyridyl)-2-pyrimidineamine (A)

To a suspension of 10.0 g (0.065 mol) of 2-amino-4-nitrotoluene in ethanol (20 ml) was added 65% nitric acid (4.6 ml, 0.065 mol) dropwise at 0° C. and stirred for 10 minutes. Cyanamide (8.32 g, 0.198 mol) in water (5 ml) was added to the reaction mixture then was refluxed for 25 hours, cooled to 0° C. and filtered and washed with water to yield 2-methyl-5-nitrophenyl-guanidine nitrate.

To a mixture of 2-methyl-5-nitrophenylguanidine nitrate (25 g, 96 mmol) and 3-dimethylamino-1-(3-pyridyl)-2-propen-1-one (17 g, 96 mmol) in isopropanol (200 ml) was added sodium hydroxide (4.5 g). The reaction was refluxed for 12 hours and cooled to 0° C. The precipitate was filtered and washed with isopropanol to give N-(2-methyl-5-nitrophenyl)-4-(3-pyridyl)-2-pyrimidine-amine.

A suspension of N-(2-methyl-5-nitrophenyl)-4-(3-pyridyl)-2-pyrimidine-amine (1.5 g, 4.6 mmol) and palladium on active carbon (150 mg, 10%) in ethyl acetate (100 ml) was hydrogenated under a hydrogen atmosphere for 2 hours. The reaction was filtered and the filtrate was concentrated to give N-(5-amino-2-methylphenyl)-4-(3-pyridyl)-2-pyrimidine-amine for future use without further purification.

Preparation II: (4-hydroxyphenyl)-N-{4-methyl-3-[(4-(3-pyridyl)pyrimidin-2-yl)-amino]phenyl}carboxamide (Z)

To a mixture of 4-hydroxybenzoic acid (10 mmol) and (A) (10 mmol) in DMF (40 ml) was added EDC (12.5 mmol) and HOBt (10 mmol). The reaction was stirred at RT for 4 hours and diluted with DCM (100 ml). The mixture was washed with water three times and dried with $Na_2SO_4$. The solution was evaporated and the residue was further purified by column chromatography to give the title compound (Z).

EXAMPLE 1

Preparation of [4-(2-aminoethoxy)phenyl]-N-{4-methyl-3-[(4-(3-pyridyl)-pyrimidin-2-yl)amino]phenyl}carboxamide To a mixture of N-BOC-aminoethnol (160 mg; 1 mmol) and (4-hydroxyphenyl)-N-{4-methyl-3-[(4-(3-pyridyl)pyrimidin-2-yl)amino]phenyl}carbox-amide [(Z), 0.85 mmol] in DCM (25 ml) was added DEAD (40% in Toluene, 1.2 mmol) and stirred at RT for four hours. To the reaction, water was added and extracted with DCM two more times. The combined organic layer was washed with water followed by brine and dried with $Na_2SO_4$. The solution was evaporated under reduced pressure and the residue was purified by column chromatography to give [4-(2-Boc-aminoethoxy)phenyl]-N-{4-methyl-3-[(4-(3-pyridyl)pyrimidin-2-yl)amino]phenyl}carboxamide that was mixed with 4N HCl in dioxane and stirred at RT for two hours. The reaction was evaporated and mixed with $NaHCO_3$ solution and extracted with EtOAc two times. The combined organic layer was washed with water followed by brine and dried with $Na_2SO_4$. The solution was evaporated to give the title compound. Mass: (M+1), 441.

EXAMPLE 2

Preparation of N-{4-methyl-3-[(4-(3-pyridyl)pyrimidin-2-yl)amino]phenyl}{4-[(1 -methylpyrrolidin-3-yl)amino]phenyl}carboxamide (4-Nitrophenyl)-N-{4-methyl-3 -[(4-(3-pyridyl)pyrimidin-2-yl)-amino]phenyl}-carboxamide was prepared analogously according to the procedures described in Preparation II using 4-nitrobenzoic acid instead of 4-hydroxybenzoic acid.

The above nitro compound was hydrogenated under hydrogen atomosphere in EtOH for 1 hour and filtered through Celite. To the solution was added NaBHCN (1.3 eq) and 1-methyl-3-pyrrolidinone (1 eq), the reaction was stirred at RT overnight and evaporated in vacuo and further purified by flash chromatography on silica gel afforded title compound. Mass: (M+1), 480.

EXAMPLE 3

Preparation of [4-(fluoropiperazinylmethyl)phenyl]-N-{4-methyl-3-[(4-(3-pyridyl)-pyrimidin-2-yl)amino]phenyl}carboxamide To the mixture of ethyl (4-hydroxymethyl)benzonate (5 mmol) in DCM (30 ml) at −78° C. was added $(CH_3OCH_2CH_2)_2NSF_3$ (5.5 mmol), the reaction was stirred at −78° C. for 2 hours and poured into saturated $NaHCO_3$. It was extracted into DCM (2×30 ml), dried ($Na_2SO_4$) and evaporated in vacuo. Flash chromatography on silica gel afforded ethyl (4-fluoromethyl)benzonate.

(4-Fluoromethyl)benzonate (2 mmol) was mixed with NBS (2.3 mmol) in $CCl_4$ and the mixture was stirred and refluxed for 6 hours and cooled to RT. The reaction was evaporated in vacuo and purified by flash chromatography on silica gel afforded ethyl (4-fluorobromomethyl)benzonate.

Ethyl (4-fluorobromomethyl)benzonate (1 mmol) was mixed with N-Boc-piperazine (1.5 mmol) in EtOH and the mixture was stirred and heated at 50° C. for two hours. The reaction was evaporated in vacuo and purified by flash chromatography on silica gel afforded ethyl (4-fluoro-N-Boc-piperazinyl-methyl)benzonate that was hydrolyzed with 2N NaOH (1.3 eq) in EtOH at RT afforded (4-fluoro-N-Boc-piperazinylmethyl)benzoic acid.

The title compound then was prepared analogously according to the procedures described in Preparation II followed by Boc-deprotection and work-up procedures described in Example 1. Mass: (M+1), 498.

EXAMPLE 4

Preparation of N-{4-methyl-3 -[(4-(3-pyridyl)pyrimidin-2-yl)amino]phenyl}-{4-[(1-methylpyrrolidin-2-yl)methoxy]phenyl}carboxamide The title compound was prepared analogously according to the procedures described in Example 1 using (1-methylpyrrolidin-2-yl)methanol instead of N-BOC-aminoethnol. Mass: (M+1), 495.

EXAMPLE 5

Preparation of N-{4-methyl-3-[(4-(3-pyridyl)pyrimidin-2-yl)amino]phenyl}[4-(pyrrolidin-3-ylamino)phenyl]carboxamide (4-Nitrophenyl)-N-{4-methyl-3-[(4-(3-pyridyl)pyrimidin-2-yl)-amino]phenyl}-carboxamide was prepared analogously according to the procedures described in Preparation II using 4-nitrobenzoic acid instead of 4-hydroxybenzoic acid.

The above nitro compound was hydrogenated under hydrogen atomosphere in EtOH for 1 hour and filtered through Celite. To the solution was added NaBHCN (1.3 eq) and 1-benzyl-3-pyrrolidinone (1 eq), the reaction was stirred at RT overnight and evaporated in vacuo and further purified by flash chromatography on silica gel afforded N-{4-methyl-3-[(4-(3-pyridyl)pyrimidin-2-yl)amino]phenyl}[4-(N-benzylpyrrolidin-3-ylamino)phenyl]carboxamide that was hydrogenated to remove benzyl protection at 50 psi in EtOH catalized by Pd/C (10%) to give the title compound. Mass: (M+1), 466.

EXAMPLE 6

Preparation of [4-(aminofluoromethyl)phenyl]-N-{4-methyl-3-[(4-(3-pyridyl)-pyrimidin-2-yl)amino]phenyl}carboxamide The title compound was prepared analogously according to the procedures described in Example 3 using ammonia instead of N-Boc-piperazine. Mass: (M+1), 429.

EXAMPLE 7

Preparation of N-{4-methyl-3-[(4-(3-pyridyl)pyrimidin-2-yl)amino]phenyl}[4-(methylpyrrolidin-3-ylamino)phenyl]carboxamide The intermediate prepared from Example 5 that was N-{4-methyl-3-[(4-(3-pyridyl)pyrimidin-2-yl)amino]phenyl}[4-(N-benzylpyrrolidin-3-ylamino)phenyl]-carboxamide was methylated via reductive amination with HCHO/NaBHCN (1.5 eq) and further hydrogenated to remove benzyl protection at 50 psi in EtOH catalized by Pd/C (10%) overnight to give the title compound. Mass: (M+1), 480.

EXAMPLE 8

Preparation of {4-[fluoro(4-methylpiperazinyl)methyl]phenyl}-N-{4-methyl-3-[(4-(3-pyridyl)pyrimidin-2-yl)amino]phenyl}carboxamide The title compound was prepared analogously according to the procedures described in Example 3 using N-methylpiperazine instead of N-Boc-piperazine. Mass: (M+1), 512.

EXAMPLE 9

Preparation of [4-(aminodifluoromethyl)phenyl]-N-{4-methyl-3-[(4-(3-pyridyl)pyrimidin-2-yl)amino]phenyl}carboxamide The title compound was prepared analogously according to the procedures described in Example 3 and 6 using methyl 4-formybenzonate instead of ethyl (4-hydroxymethyl)benzonate. Mass: (M+1), 447.

EXAMPLE 10

Preparation of {4-[methyl(1-methylpyrrolidin-3-yl)amino]phenyl}-N-{4-methyl-3-[(4-(3-pyridyl)pyrimidin-2-yl)amino]phenyl}carboxamide The product from Example 7 was methylated via reductive amination with HCHO/NaBHCN (1.5 eq) to give the title compound. Mass: (M+1), 494.

EXAMPLE 11

Preparation of (4-{fluoro[(1-methylpyrrolidin-3-yl)amino]methyl}phenyl)-N-{4-methyl-3-[(4-(3-pyridyl)pyrimidin-2-yl)amino]phenyl}carboxamide The product from Example 6 was reacted with N-methyl-3-pyrrolidione and NABHCN in DCM to give the title compound. Mass: (M+1), 512.

EXAMPLE 12

Preparation of {4-[fluoro(methylpyrrolidin-3-ylamino)methyl]phenyl}-N-{4-methyl-3-[(4-(3-pyridyl)pyrimidin-2-yl)amino]phenyl}carboxamide The product from Example 6 was reacted with 1-benzyl-3-pyrrolidinone and NABHCN in DCM to give {4-[fluoro(benzylpyrrolidin-3-ylamino)methyl]-phenyl}-N-{4-methyl-3-[(4-(3-pyridyl)pyrimidin-2-yl)amino]phenyl}carboxamide that was methylated via reductive amination with HCHO/NaBHCN and further hydrogenated to remove benzyl group at 50 psi in EtOH catalized by Pd/C (10%) overnight to afford the title compound. Mass: (M+1), 512.

EXAMPLE 13

Preparation of [4-({[2-(dimethylamino)ethyl]amino}fluoromethyl)phenyl]-N-{4-methyl-3-[(4-(3-pyridyl)pyrimidin-2-yl)amino]phenyl}carboxamide The title compound was prepared analogously according to the procedures described in Example 3 using N,N,-dimethylethylenediamine instead of N-Boc-piperazine. Mass: (M+1), 500.

EXAMPLE 14

Preparation of [4-(difluoropiperazinylmethyl)phenyl]-N-{4-methyl-3-[(4-(3-pyridyl)pyrimidin-2-yl)amino]phenyl}carboxamide The title compound was prepared analogously according to the procedures described in Example 3 using methyl 4-formybenzonate instead of ethyl (4-hydroxymethyl)benzonate. Mass: (M+1), 516.

EXAMPLE 15

Preparation of {4-[difluoro(4-methylpiperazinyl)methyl]phenyl}-N-{4-methyl-3-[(4-(3-pyridyl)pyrimidin-2-yl)amino]phenyl}carboxamide The title compound was prepared analogously according to the procedures described in Example 14 using N-methylpiperazine instead of N-Boc-piperazine. Mass: (M+1), 530.

EXAMPLE 16

Preparation of [4-({[2-(dimethylamino)ethyl]amino}difluoromethyl)phenyl]-N-{4-methyl-3-[(4-(3-pyridyl)pyrimidin-2-yl)amino]phenyl}carboxamide The title compound was prepared analogously according to the procedures described in Example 14 using N,N,-dimethylethylenediamine instead of N-Boc-piperazine. Mass: (M+1), 518.

EXAMPLE 17

Preparation of (4-{fluoro[methyl(1-methylpyrrolidin-3-yl)amino]methyl}-phenyl)-N-{4-methyl-3-[(4-(3-pyridyl)pyrimidin-2-yl)amino]phenyl}carboxamide The product from Example 11 was methylated via reductive amination with HCHO/NaBHCN afforded the title compound. Mass: (M+1), 526.

EXAMPLE 18

Preparation of {4-[fluoro(pyrrolidin-3-ylamino)methyl]phenyl}-N-{4-methyl-3-[(4-(3-pyridyl)pyrimidin-2-yl)amino]phenyl}carboxamide {4-[Fluoro(benzylpyrrolidin-3-ylamino)methyl]phenyl}-N-{4-methyl-3-[(4-(3-pyridyl)pyrimidin-2-yl)amino]phenyl}carboxamide from Example 12 hydrogenated to remove benzyl protection at 50 psi in EtOH catalyzed by Pd/C (10%) overnight to afford the title compound. Mass: (M+1), 498.

EXAMPLE 19

Preparation of {4-[(4-ethylpiperazinyl)difluoromethyl]phenyl}-N-{4-methyl-3-[(4-(3-pyridyl)pyrimidin-2-yl)amino]phenyl}carboxamide The product from Example 14 was ethylated via reductive amination with $CH_3CHO$/NaBHCN afforded the title compound. Mass: (M+1), 544.

EXAMPLE 20

Preparation of {4-[(4-ethylpiperazinyl)fluoromethyl]phenyl}-N-{4-methyl-3-[(4-(3-pyridyl)pyrimidin-2-yl)amino]phenyl}carboxamide The product from Example 3 was ethylated via reductive amination with $CH_3CHO$/NaBHCN afforded the title compound. Mass: (M+1), 526.

EXAMPLE 21

Preparation of (4-{difluoro[methyl(1-methylpyrrolidin-3-yl)amino]methyl}-phenyl)-N-{4-methyl-3-[(4-(3-pyridyl)pyrimidin-2-yl)amino]phenyl}carboxamide The title compound was prepared from the product in Example 9 according to the similar procedures described in Example 17. Mass: (M+1), 544.

EXAMPLE 22

Preparation of {4-[difluoro(methylpyrrolidin-3-ylamino)methyl]phenyl}-N-{4-methyl-3-[(4-(3-pyridyl)pyrimidin-2-yl)amino]phenyl}carboxamide The title compound was prepared from the product in Example 9 according to the similar procedures described in Example 12. Mass: (M+1), 530.

EXAMPLE 23

Preparation of [4-({[2-(dimethylamino)ethyl]amino}fluoromethyl)phenyl]-N-{4-methyl-3-[(4-(3-pyridyl)pyrimidin-2-yl)amino]phenyl}carboxamide The title compound was prepared from the product in Example 9 according to the similar procedures described in Example 11. Mass: (M+1), 530.

EXAMPLE 24

Preparation of {4-[difluoro(pyrrolidin-3-ylamino)methyl]phenyl}-N-{4-methyl-3-[(4-(3-pyridyl)pyrimidin-2-yl)amino]phenyl}carboxamide The title compound was prepared from the product in Example 9 according to the similar procedures described in Example 18. Mass: (M+1), 516.

EXAMPLE 25

Preparation of (4-{[methyl(1-methylpyrrolidin-3-yl)amino]methyl}phenyl)-N-{4-methyl-3-[(4-(3-pyridyl)pyrimidin-2-yl)amino]phenyl}carboxamide 4-(BOC-aminomethyl)benzoic acid was used instead of 4-hydroxybenzoic acid in the procedures described in Preparation II, followed by deprotection of Boc group with 4N HCl/Dioxane to give [4-(aminomethyl)phenyl]-N-{4-methyl-3-[(4-(3-pyridyl)-pyrimidin-2-yl)amino]phenyl}carboxamide.

The title compound was prepared analogously according to the procedures described in Example 21 using [4-(aminomethyl)phenyl]-N-{4-methyl-3-[(4-(3-pyridyl)-pyrimidin-2-yl)amino]phenyl}carboxamide instead of the product from Example 9. Mass: (M+1), 508.

EXAMPLE 26

Preparation of {4-(methylpyrrolidin-3-ylamino)methylphenyl}-N-{4-methyl-3-[(4-(3-pyridyl)pyrimidin-2-yl)amino]phenyl}carboxamide The title compound was prepared analogously according to the procedures described in Example 22 using [4-(aminomethyl)phenyl]-N-{4-methyl-3-[(4-(3-pyridyl)-pyrimidin-2-yl)amino]phenyl}carboxamide instead of the product from Example 9. Mass: (M+1), 494.

EXAMPLE 27

Preparation of (4-{[(1-methylpyrrolidin-3-yl)amino]methyl}phenyl)-N-{4-methyl-3-[(4-(3-pyridyl)pyrimidin-2-yl)amino]phenyl}carboxamide The title compound was prepared analogously according to the procedures described in Example 23 using [4-(aminomethyl)phenyl]-N-{4-methyl-3-[(4-(3-pyridyl)-pyrimidin-2-yl)amino]phenyl}carboxamide instead of the product from Example 9. Mass: (M+1), 494.

EXAMPLE 28

Preparation of {4-(pyrrolidin-3-ylamino)methylphenyl}-N-{4-methyl-3-[(4-(3-pyridyl)pyrimidin-2-yl)amino]phenyl}carboxamide The title compound was prepared analogously according to the procedures described in Example 24 using [4-(aminomethyl)phenyl]-N-{4-methyl-3-[(4-(3-pyridyl)-pyrimidin-2-yl)amino]phenyl}carboxamide instead of the product from Example 9. Mass: (M+1), 480.

What is claimed is:

1. A phenylaminopyrlmidine compound of formula (I)

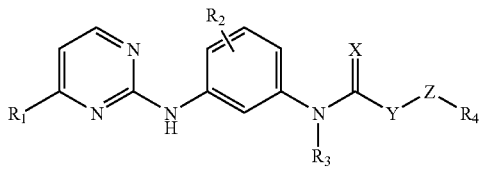

Formula (I)

Wherein

X is oxygen or sulfur,

Y is a direct bond, oxygen, nitrogen or lower alkyl,

Z is an aliphatic, cycloaliphatic, aryl or a heterocyclyl radical, $R_1$ is heterocyclyl radical, $R_2$ is hydrogen, halogen, halogenlower alkyl, lower alkyl or lower alkoxyl, $R_3$ is hydrogen or lower alkyl, $R_4$ is oxy-lower alkylamino, lower alkyl oxy-lower alkylamino, oxyheterocyclyl, oxy-lower alkylheterocyclyl, lower alkyl oxy-lower alkylheterocyclyl, halogenlower alkylamino, halogenlower alkylheterocyclyl, lower alkylamino lower alkylamino, amino lower alkylheterocyclyl or lower alkylamino lower alkylheterocyclyl, or a pharmaceutically acceptable salt thereof.

2. A compound of Formula (I) according to claim 1, wherein

X is oxygen or sulfur,

Y is a direct bond, oxygen, nitrogen or lower alkyl,

Z is an aliphatic, cycloaliphatic, aryl or a heterocyclyl radical, $R_1$ is heterocyclyl radical, $R_2$ is hydrogen, halogen, halogenlower alkyl, lower alkyl or lower alkoxyl, $R_3$ is hydrogen or lower alkyl, $R_4$ is:

(a) oxy-lower alkyl unsubstituted, mono or disubstituted amino; oxy-lower alkyl morpholinyl, oxy-lower alkyl pyrrolidinyl, oxy-lower alkyl piperidinyl, oxy-lower alkyl piperazinyl, oxy-pyrrolidinyl, oxy-piperidinyl, (b) lower alkyl oxy-lower alkyl unsubstituted, mono or disubstituted amino; lower alkyl oxy-lower alkyl morpholinyl, lower alkyl oxy-lower alkyl pyrrolidinyl, lower alkyl oxy-lower alkyl piperidinyl, lower alkyl oxy-lower alkyl piperazinyl, (c) mono or difluoro substituted lower alkyl unsubstituted, mono or disubstituted amino; mono or difluoro substituted lower alkyl morpholinyl, mono or difluoro substituted lower alkyl pyzrolidinyl, mono or difluoro substituted lower alkyl piperidinyl, mono or difluoro substituted lower alkyl piperazinyl, (d) amino lower alkyl morpholinyl, amino lower alkyl pyrrolidinyl, amino lower alkyl piperidinyl, amino lower alkyl piperazinyl, (e) lower alkylamino lower alkyl unsubstituted, mono or disubstituted amino; lower alkylamino lower alkyl morpholinyl, lower alkylamino lower alkyl pyrrolidinyl, lower alkylamino lower alkyl piperidinyl, lower alkylamino lower alkyl piperazinyl, or a pharmaceutically acceptable salt thereof.

3. A compound of Fonnula (I) according to claim 1, wherein

X is oxygen or sulfur,

Y is a direct bond,

Z is an aliphatic, cycloaliphatic, aryl or a heterocyclyl radical, $R_1$ is heterocyclyl radical, $R_2$ is hydrogen, halogen, halogenlower alkyl, lower alkyl or lower alkoxyl, $R_3$ is hydrogen or lower alkyl, $R_4$ is:

(a) oxy-lower alkyl unsubstituted, mono or disubstituted amino; oxy-lower alkyl morpholinyl, oxy-lower alkyl pyrrolidinyl, oxy-lower alkyl piperidinyl, oxy-lower alkyl piperazinyl, oxy-pyrrolidinyl, oxy-piperidinyl, (b) lower alkyl oxy-lower alkyl unsubstituted, mono or disubstituted amino; lower alkyl oxy-lower alkyl morpholinyl, lower alkyl oxy-lower alkyl pyrrolidinyl, lower alkyl oxy-lower alkyl piperidinyl, lower alkyl oxy-lower alkyl piperazinyl, (c) mono or difluoro substituted lower alkyl unsubstituted, mono or disubstituted amino; mono or difluoro substituted lower alkyl morpholinyl, mono or difluoro substituted lower alkyl pyrrolidinyl, mono or difluoro substituted lower alkyl piperidinyl, mono or difluoro substituted lower alkyl piperazinyl, (d) amino lower alkyl morpholinyl, amino lower alkyl pyrrolidinyl, amino lower alkyl piperidinyl, amino lower alkyl piperazinyl, (e) lower alkylamino lower alkyl unsubstituted, mono or disubstituted amino; lower alkylamino lower alkyl morpholinyl, lower alkylamino lower alkyl pyrrolidinyl, lower alkylamino lower alkyl piperidinyl, lower alkylamino lower alkyl piperazinyl, or a pharmaceutically acceptable salt thereof.

4. A compound of Formula (I) according to claim 1, wherein

X is oxygen or sulfur,

Y is a direct bond,

Z is aryl, $R_1$ is heterocyclyl radical, $R_2$ is hydrogen, halogen, halogenlower alkyl, lower alkyl or lower alkoxyl, $R_3$ is hydrogen or lower alkyl, $R_4$ is:

(a) oxy-lower alkyl unsubstituted, mono or disubstituted amino; oxy-lower alkyl morpholinyl, oxy-lower alkyl pyrrolidinyl, oxy-lower alkyl piperidinyl, oxy-lower alkyl piperazinyl, oxy-pyrrolidinyl, oxy-piperidinyl, (b) lower alkyl oxy-lower alkyl unsubstituted, mono or disubstituted amino; lower alkyl oxy-lower alkyl morpholinyl, lower alkyl oxy-lower alkyl pyrrolidinyl, lower alkyl oxy-lower alkyl piperidinyl, lower alky) oxy-lower alkyl piperazinyl, (c) mono or difluoro substituted lower alkyl unsubstituted, mono or disubstituted amino; mono or difluoro substituted lower alkyl morpholinyl, mono or difluoro substituted lower alkyl pyrrolidinyl, mono or difluoro substituted lower alkyl piperidinyl, mono or difluoro substituted lower alkyl piperazinyl,
(d) amino lower alkyl morpholinyl, amino lower alkyl pyrrolidinyl, amino lower alkyl piperidinyl, amino lower alkyl piperazinyl,
(e) lower alkylamino lower alkyl unsubstituted, mono or disubstituted amino; lower alkylamino lower alkyl morpholinyl, lower alkylamino lower alkyl pyrrolidinyl, lower alkylamino lower alkyl piperidinyl, lower aikylamino lower alkyl piperazinyl, or a pharmaceutically acceptable salt thereof.

5. A compound of Formula (I) according to claim 1, wherein
X is oxygen or sulfur,
Y is a direct bond,
Z Is aryl,
$R_1$ is heterocyclyl radical,
$R_2$ is halogenlower alkyl or lower alkyl,
$R_3$ is hydrogen or lower alkyl,
$R_4$ is:
(a) oxy-lower alkyl unsubstituted, mono or disubstituted amino; oxy-lower alkyl morpholinyl, oxy-lower alkyl pyrrolidinyl, oxy-lower alkyl piperidinyl, oxy-lower alkyl piperazinyl, oxy-pyrrolidinyl, oxy-piperidinyl,
(b) lower alkyl oxy-lower alkyl unsubstituted, mono or disubstituted amino; lower alkyl oxy-lower alkyl morpholinyl, lower alkyl oxy-lower alkyl pyrrolidinyl, lower alkyl oxy-lower alkyl piperidinyl, lower alkyl oxy-lower alkyl piperazinyl,
(c) mono or difluoro substituted lower alkyl unsubstituted, mono or disubstituted amino; mono or difluoro substituted lower alkyl morpholinyl, mono or difluoro substituted lower alkyl pyrrolidinyl, mono or difluoro substituted lower alkyl piperidinyl, mono or difluoro substituted lower alkyl piperazinyl,
(d) amino lower alkyl morpholinyl, amino lower alkyl pyrrolidinyl, amino lower alkyl piperidinyl, amino lower alkyl piperazinyl,
(e) lower alkylamino lower alkyl unsubstituted, mono or disubstituted amino; lower alkylamino lower alkyl morpholinyl, lower alkylamino lower alkyl pyrrolidinyl, lower alkylamino lower alkyl piperidiny, lower alkylamino lower alkyl piperazinyl, or a pharmaceutically acceptable salt thereof.

6. A compound of Formula (I) according to claim 1, wherein
X is oxygen or sulfur,
Y is a direct bond,
Z is aryl,
$R_1$ is heterocyclyl radical,
$R_2$ is lower alkyl,
$R_3$ is hydrogen,
$R_4$ is:
(a) oxy-lower alkyl unsubstituted, mono or disubstituted amino; oxy-lower alkyl morpholinyl, oxy-lower alkyl pyrrolidinyl, oxy-lower alkyl piperidinyl, oxy-lower alkyl piperazinyl, oxy-pyrrolidinyl, oxy-piperidinyl,
(b) lower alkyl oxy-lower alkyl unsubstituted, mono or disubstituted amino; lower alkyl oxy-lower alkyl morpholinyl, lower alkyl oxy-lower alkyl pyrrolidinyl, lower alkyl oxy-lower alkyl piperidinyl, lower alkyl oxy-lower alkyl piperazinyl,
(c) mono or difluoro substituted lower alkyl unsubstituted, mono or disubstituted amino; mono or difluoro substituted lower alkyl morpholinyl, mono or difluoro substituted lower alkyl pyrrolidinyl mono or difluoro substituted lower alkyl piperidinyl, mono or difluoro substituted lower alkyl piperazinyl,
(d) amino lower alkyl morpholnyl, amino lower alkyl pyrrolidinyl, amino lower alkyl piperidinyl, amino lower alkyl piperazinyl,
(e) lower alkylamino lower alkyl unsubstituted, mono or disubstituted amino; lower alkylamino lower alkyl morpholinyl, lower alkylamino lower alkyl pyrrolidinyl, lower alkylamino lower alkyl piperidinyl, lower alkylamino lower alkyl piperazinyl, or a pharmaceutically acceptable salt thereof.

7. A compound of Formula (I) according to claim 1, wherein
X is oxygen,
Y is a direct bond,
Z is phenyl,
$R_1$ is: 3-pyridyl or 4-pyridyl
$R_2$ is: methyl, F, Cl or hydrogen,
$R_3$ is hydrogen, $R_4$ is:

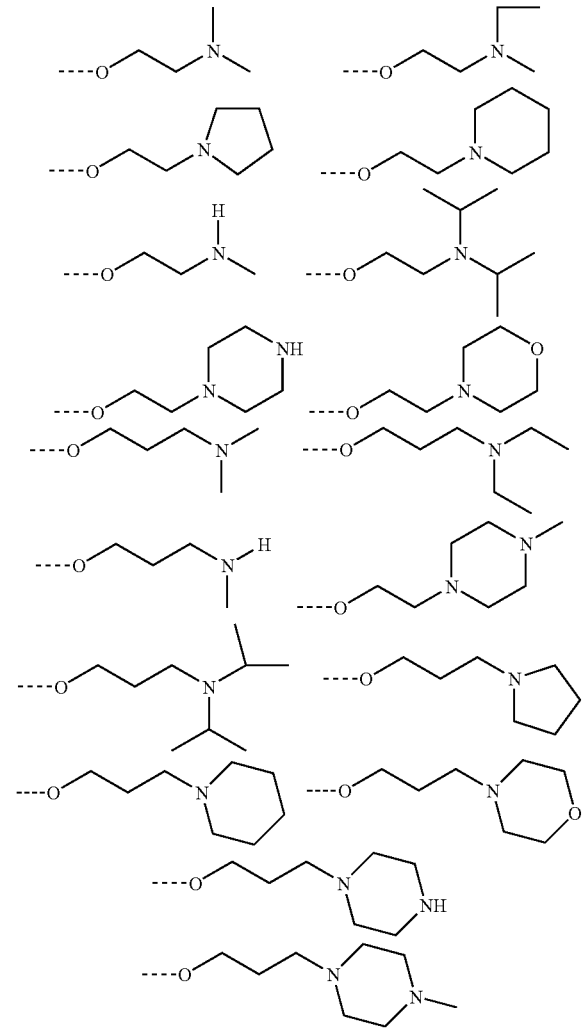

-continued
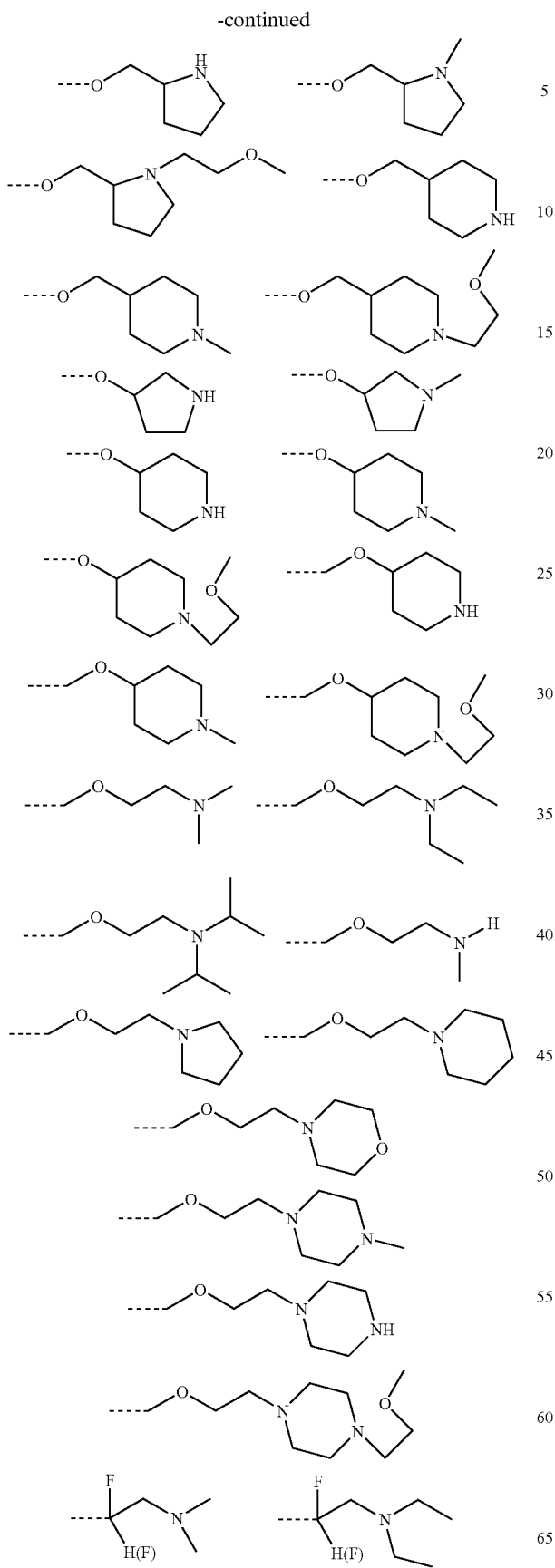
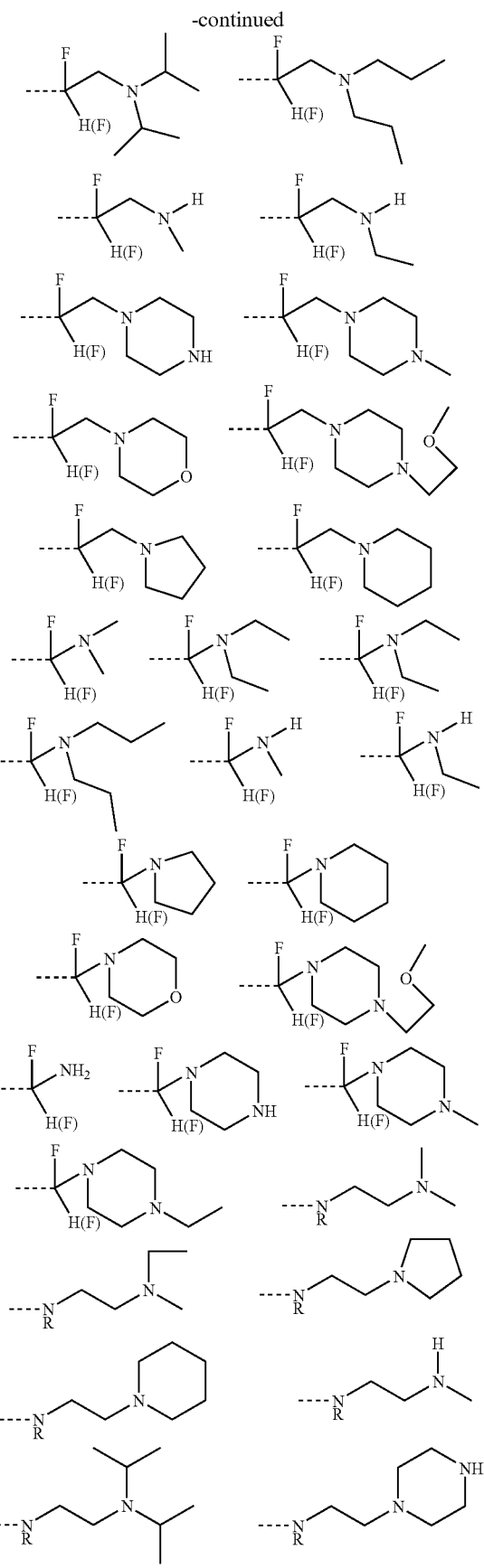

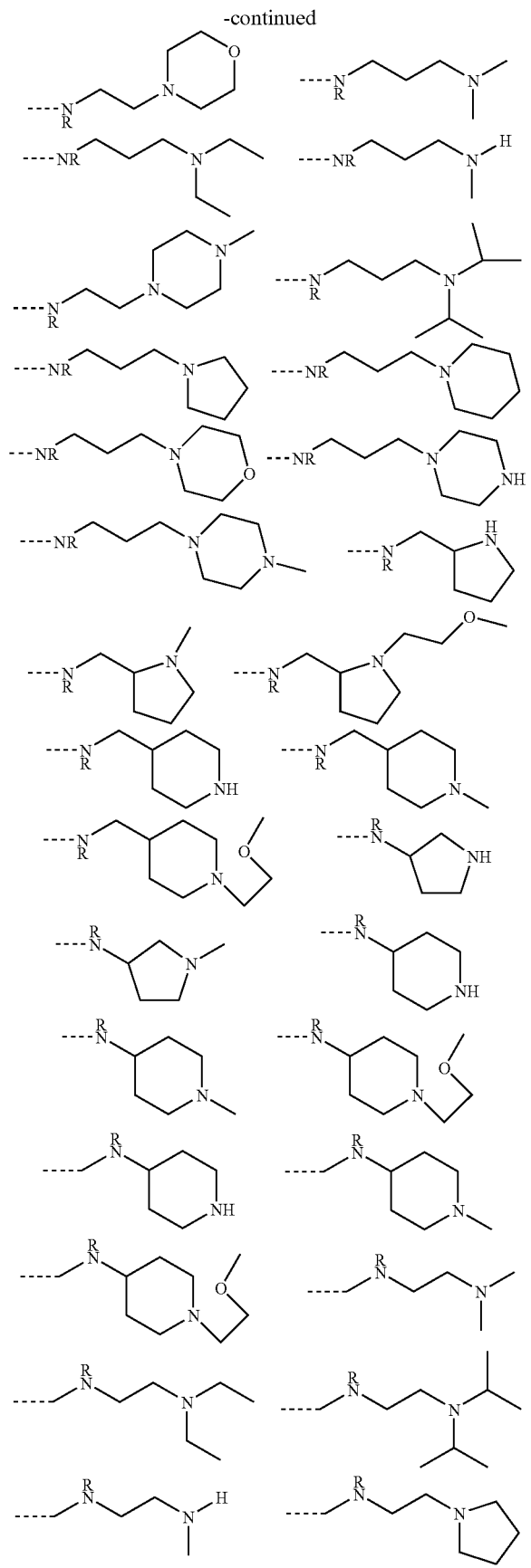

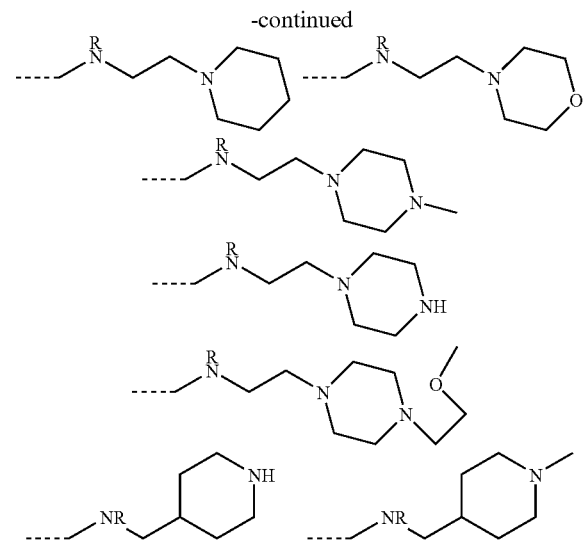

$R_4$ is (cont'd):

$R_4$ is (cont'd):

R is hydrogen, lower alkyl, aliphatic, or cycloaliphatic-radicals, or a pharmaceutically acceptable salt thereof.

8. A compound of Formula (I) according to claim 1 is selected from:

[4-(2-aminoethoxy)phenyl]-N-{4-methyl-3-[(4-(3-pyridyl)-pyrimidin-2-yl)amino]phenyl}carboxamide

[4-(fluoropiperazinylmethyl)phenyl]-N-{4-methyl-3-[(4-(3-pyridy)-pyrimidin-2-yl)amino]phenyl}carboxamide N-{4-methyl-3-[(4-(3-pyridyl)pyrimidin-2-yl)amino]phenyl}-{4-[(1-methylpyrrolidin-2-yl)methoxy]phenyl}carboxamide

[4-(aminofluoromethyl)phenyl]-N-{4-methyl-3-[(4-(3-pyridyl)pyrimidin-2-yl)amino]phenyl}carboxamide {4-[fluoro(4-methylpiperazinyl)methyl]phenyl}-N-{4-methyl-3-[(4-(3-pyridyl)pyrimidin-2-yl)amino]phenyl}carboxamide

[4-(aminodifluoromethyl)phenyl]-N-{4-methyl-3-[(4-(3-pyridyl)pyrimidin-2-yl)amino]phenyl}carboxamide (4-{fluoro[(1-methylpyrrolidin)-3-yl)amino]methyl}phenyl)-N-{4-methyl-3-[(4-(3-pyridyl)pyrimidin-2-yl)amino]phenyl}carboxamide {4-[fluoro(methypyrrolidin-3-ylamino)methyl]phenyl}-N-{4-methyl-3-[(4-3-pyridyl)pyrimidin-2-yl)amino]phenyl}carboxamide

[4-({[2-(dimethylamino)ethyl]amino}fluoromethyl)phenyl]-N-{4-methyl-3-[(4-(3-pyridyl)pyrimidin-2-yl)amino]phenyl}carboxamide

[4-(difluoropiperazinylmethyl)phenyl]-N-{4-methyl-3-[(4-(3-pyridyl)pyrimidin-2-yl)amino]phenyl}carboxamide {4-[difluoro(4-methylpiperazinyl)methyl]phenyl}-N-{4-methyl-3-[(4-(3-pyridyl)pyrimidin-2-yl)amino]phenyl}carboxamide

[4-({[2-(dimethylamino)ethyl]amino}difluoromethyl)phenyl]-N-{4-methyl-3-[(4-(3-pyridyl)pyrimidin-2-yl)amino]pbenyl}carboxamide (4-{fluoro[methyl(1-methylpyrrolidin-3-yl)amino]methyl}-phenyl)-N-{4-methyl-3-[(4-(3-pyridyl)pyrimidin-2-yl)amino]phenyl}carboxamide {4-[fluoro(pyrrolidin-3-ylamino)methyl]phenyl}-N-{4-methyl-3-[(4-(3-pyridyl)pyrimidin-2-yl)amino]phenyl}carboxamide {4-[(4-ethylpipeazinyl)difluoromethyl]phenyl}-N-{4-methyl-3-[(4-(3-pyridyl)pyrimidin -2-yl)amino]phenyl}carboxamide {4-[(4-ethylpiperazinyl)fluoromethyl]phenyl}-N-{4-methyl-3-[(4-(3-(pyridyl)pyrimidin -2-yl)amino]phenyl}carboxamide (4-{(difluoro[methyl(1-methylpyrrolidin-3-yl)amino]methyl}-phenyl)-N-{4-methyl-3-[(4-(3-pyridyl)pyrimidin-2-yl)amino]phenyl}carboxamide {4-[difluoro(metlylpyrrolidin-3-ylamino)methyl]phenyl}-N-{(4-methyl-3-[(4-(3-pyridyl)pyrimidin-2-yl)amino]phenyl}carboxamide

[4-({[2-(dimethylamino)ethyl]amino}fluoromethyl)phenyl]-N-{4-methyl-3-[(4-(3-pyridyl)pyrimidin-2-yl)amino]phenyl}caxboxamide {4-[difluoro(pyrrolidin-3-ylamino)methyl]phenyl}-N-{4-methyl-3-[(4-(3-pyridyl)pyrimidin-2-yl)amino]phenyl}caboxamide or a pharmaceutically acceptable salt thereof.

9. A pharmaceutical acceptable salt according to any one of claims 1 to 8 is methanesulfonic acid salt.

* * * * *